United States Patent
Soikum et al.

(10) Patent No.: US 9,629,912 B2
(45) Date of Patent: Apr. 25, 2017

(54) METHOD, DEVICE AND SYSTEM FOR TARGETTED CELL LYSIS

(75) Inventors: Soiwisa Soikum, Ayutthaya (TH); Lars Thomsen, Ayutthaya (TH); John Robert Dodgson, London (GB)

(73) Assignees: William H. Bollman, Bethesda, MD (US); TMB LABS LTD., Hongkong (CN)

( * ) Notice: Subject to any disclaimer, the term of this patent is extended or adjusted under 35 U.S.C. 154(b) by 861 days.

(21) Appl. No.: 13/643,695

(22) PCT Filed: Apr. 26, 2011

(86) PCT No.: PCT/GB2011/000645
§ 371 (c)(1),
(2), (4) Date: Jun. 3, 2013

(87) PCT Pub. No.: WO2011/135294
PCT Pub. Date: Nov. 3, 2011

(65) Prior Publication Data
US 2013/0261683 A1    Oct. 3, 2013

(30) Foreign Application Priority Data

Apr. 26, 2010 (GB) .................................. 1006841.9
Oct. 4, 2010 (GB) .................................. 1016582.7

(51) Int. Cl.
*A61N 1/00* (2006.01)
*A61K 41/00* (2006.01)
(Continued)

(52) U.S. Cl.
CPC .......... *A61K 41/0038* (2013.01); *A61N 1/327* (2013.01); *C12N 13/00* (2013.01); *A61B 18/18* (2013.01); *A61N 2/00* (2013.01)

(58) Field of Classification Search
CPC ... A61N 1/00; A61N 1/06; A61N 1/10; A61N 1/18; A61N 1/40; A61N 2/00; A61N 2/04; A61N 2/10
See application file for complete search history.

(56) References Cited

U.S. PATENT DOCUMENTS 4,767,611 A     8/1988  Gordon
2010/0029785 A1  2/2010  Decuzzi

FOREIGN PATENT DOCUMENTS

WO   WO2008/062378   5/2008
WO   WO2010/151277   12/2010

OTHER PUBLICATIONS

Wang et al.,Dynamic Superconcentration at Critical-Point Double-Layer Gates of Conducting Nanoporous Granules Due to Asymmetric Tangential Fluxes, Biomicrofludics, 2008. pp. 014102-1 through 014102-9.
(Continued)

*Primary Examiner* — Edward Moran
*Assistant Examiner* — Elizabeth K So
(74) *Attorney, Agent, or Firm* — Wenderoth, Lind & Ponack, L.L.P.

(57) ABSTRACT

A method, device and system employs particles, such as nanoparticles, and an electric or electro-magnetic field, to cause cell death in target cells by non-thermal means. The method of causing targeted cell death comprises the steps of: introducing a particle to the interior of a target cell and exposing the target cell to a transient electromagnetic field for a sufficient time interval in order to cause cell death. The invention overcomes problems associated with similar methods as a result of the fact that a smaller electric field is applied because the particle enhances the effect of the electric field in its immediate vicinity, so reducing the field strength needed to achieve cell lysis and thereby reducing the risk of damage to healthy cells that may be in its vicinity.

(Continued)

Apparatus for performing the method; as well as techniques of delivering particles and for producing particles are also described.

18 Claims, 24 Drawing Sheets

(51) Int. Cl.
*A61N 1/32* (2006.01)
*C12N 13/00* (2006.01)
*A61B 18/18* (2006.01)
*A61N 2/00* (2006.01)

(56) References Cited

OTHER PUBLICATIONS

Suh et al., Nanotechnology, Nanotoxicology, and Neuroscience, Prog Neurobiol, Feb. 2009, pp. 133-170.M.
Muro et al., Control of Endothelial Targeting and Intracellular Delivery of Therapeutic Enzymes by Modulating the Size and Shape of ICAM-1-targeted Carriers, Molecular Therapy, 2008 vol. 16, pp. 1450-1458.
Zhang et al., Size Dependent Endocytosis of Nanoparticles, Adv Mater, 2009 vol. 21, pp. 419-424.
Smith et al., Model of Creation and Evolution of Stable Electropores for DNA Delivery, Biophysical Journal, May 2004 vol. 86, pp. 2813-2826.

A

B

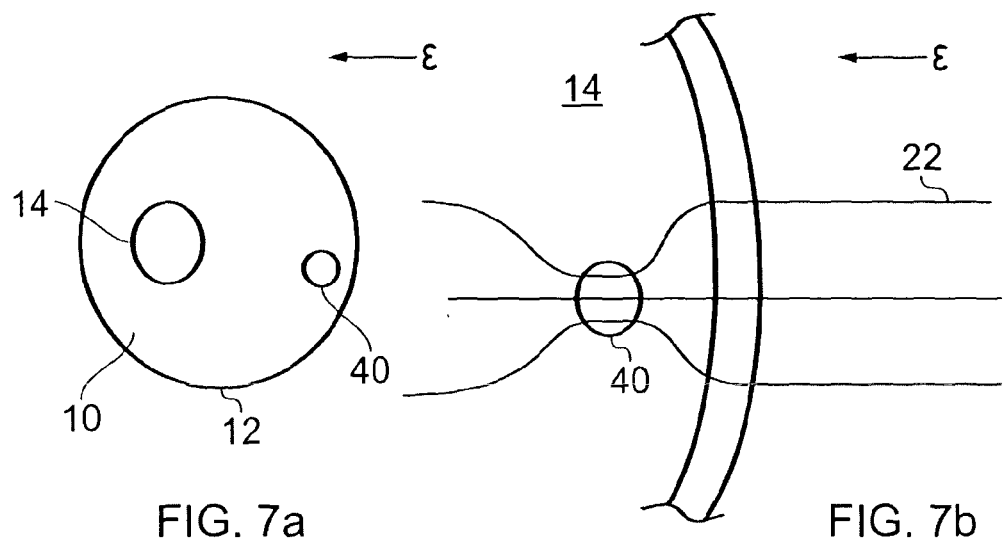
FIG. 7a
FIG. 7b
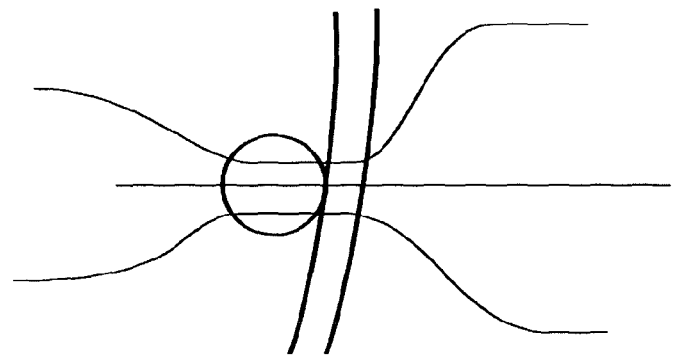
FIG. 7c
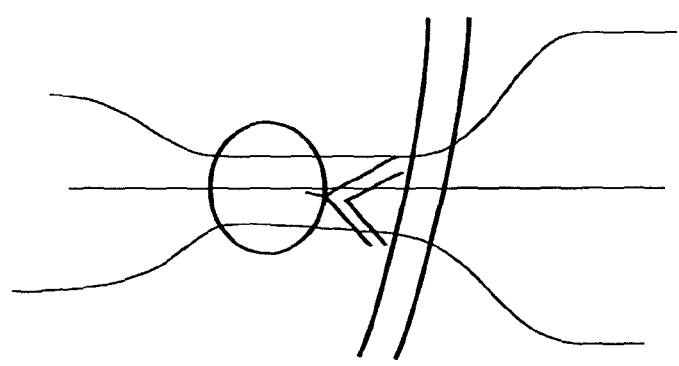
FIG. 7d

METHOD, DEVICE AND SYSTEM FOR TARGETTED CELL LYSIS

FIELD OF THE INVENTION

The present invention relates to a method, device and system for cell lysis, more particularly the invention relates to a method, device and system that employs particles, or nanoparticles, together with an electric or electro-magnetic field to cause cell death in target cells by primarily non-thermal means.

BACKGROUND OF THE INVENTION

The use of electro-magnetic fields for treatment of cancer by causing lysis to cells that harbor, or are in close proximity to particles responsive to such fields, is known. The techniques involve using a micro sized particle, typically below 0.1 µm, which for example comprises an iron oxide core and is coated with a polymer. Typically a secondary coating is applied where the particle is activated by chemicals that show specificity for biological targets of interest. The aim was to concentrate particles at the site of a biological target, where a specific chosen target can be an exclusive marker, expressed for example by cancer cells, and presented on the extracellular side of the cell. Target cells are then destroyed thermally by means of absorption of energy from the electromagnetic field.

Efforts are being made to improve techniques by focusing on factors, such as clearance of particles from blood before reaching the target cells; binding unselectively to other than target cells; toxicity of the particles in use and insufficient effect from induced electric fields to cause killing of the target cells.

PRIOR ART

International Patent Application WO-A-2010/151277 (Davalos et al) discloses a method of treating neoplasia in a subject using irreversible electroporation in which nanoparticles are administered to the subject in an amount sufficient to permit at least some of the nanoparticles to come into close proximity to the neoplastic cells. At least two electrodes are implanted into or adjacent the neoplastic cells within the body of the subject. Multiple electric pulses are then emitted from the electrodes into the neoplasia. Typically a field strength of about 500 Vcm-1 to 1500 Vcm-1, is applied between the electrodes, for a duration of 90 microseconds or less. This was shown to cause predominantly non-thermal killing of the neoplastic cells.

WO-A-2010/151277 discloses that the use of nanoparticles can reduce the threshold field for the destruction of cells by means of irreversible electroporation, and so allow an electric field to be chosen, such that cells having nanoparticles in proximity, are destroyed while those without particles remain are not destroyed. If the nanoparticles have a coating that allows them preferentially to associate with a neoplastic cell, rather than healthy cells, this allows the neoplastic cell to be destroyed while the healthy cells are undamaged.

International Patent Application WO-A-2010/151277 further discloses that use of nanoparticles may also increase the volume of the treated area around a pair of implanted electrodes over the area when nanoparticles are not used. It is stated that the mechanism of action is an enhancement of the local electric field at the cell membrane owing to the presence of the particles. A wide range of particle materials is mentioned, but only theoretical results for carbon nanotubes and insulating polystyrene spheres, and practical results for carbon nanotubes, are disclosed.

Despite the foregoing, WO-A-2010/151277 is a theoretical discussion, showing that a relatively modest field enhancement, for example when applied to insulating polystyrene beads located around a cell exterior, of approximately of a factor of 2 is achieved, as shown in Davalos FIG. 20. Carbon nanotubes were shown to aid in killing of cells in culture, but only by a modest amount (see Davalos FIG. 19) and only at high field strength (500 Vcm-1).

Further there is no specific guidance on the physical properties of the particles needed to achieve effective enhanced irreversible electroporation, save that given in Davalos FIG. 18. FIG. 18 depicts a direct current (DC) field arrangement; and shows a maximum area of 4 times (i.e. twice the characteristic dimension of the particle) in which field enhancement occurs. It is seen that the ratio of conductivity of the particle, relative to that of a surrounding medium, has a relatively small effect. Further the ratio of the permittivity of the particle, to that of the surrounding medium, has substantially no effect, on the efficacy of the method.

Therefore the field enhancement in the model described is in fact modest and so the improvement of the method disclosed is likewise modest. Furthermore no disclosure is made of a preferred mode of administration of the particles.

Another disadvantage is that the electrodes in Davalos et al need to be implanted within the body, close to or at the site of the neoplasia, which is an invasive and in some cases impractical procedure. No disclosure is made of a method that is capable of treating delocalized neoplastic cells, for example within a body fluid such as blood, for example in cases of leukemia.

The use of carbon nanotubes to reduce the field at which reversible electroporation occurs is disclosed in International Patent Application WO-A-2008/062378 (Raffa et al). The method has been shown to cause cell death resulting from the formation of irreversible pores in the membrane. The method is hereinafter referred to as irreversible electroporation.

In a poster, shown at the Nordic Naiad Symposium, Copenhagen, from 1-3 Nov. 2010, by Soikum and Thomsen, there is disclosed a method for killing bacterial cells or spores, that includes the steps of: providing at least one particle with high electrical permittivity, in close proximity to the cell membrane or cell wall, and subsequently applying an electric field. The particle acts to enhance the field in the vicinity of the particle thereby increasing the effect of the field on the cell membrane.

Soikum and Thomsen also disclose a field enhancement effect that arises as a result of use of a nanoparticle, for example that obtained when using a metal nanoparticle, adjacent the cell membrane. For example a strong field enhancement effect was observed using a pair of gold nanospheres in proximity to each other in a medium with the same relative permittivity as blood. A chip technology was used to provide means for a well-defined field, over the sample containing the target cells.

U.S. Pat. No. 4,767,611 (Gordon) discloses treatment of cancer and other diseases, including infectious diseases, through the use of electromagnetic energy deposition within the cell resulting in targeted cell death. The process comprises introducing particles into the interior of cells in living tissue. The particles are capable of affecting the intracellular conductivity, dielectric properties, dipole content and membrane characteristics of the cell and nucleus.

The method in U.S. Pat. No. 4,767,611 differs from other forms of thermal destruction of cells in that energy is deposited into the cells directly, rather than into the particles and then conducted to the cells. However, the method suffers from disadvantages, namely: a large amount of energy needs to be deposited in the cells to be destroyed, and heat is dissipated to surrounding tissues, potentially causing damage to local healthy cells.

The inventors have now improved the method for targeted cell lysis by primarily non-thermal means. They have also improved the associated apparatus.

SUMMARY OF THE INVENTION

According to a first aspect of the invention there is provided a method of causing targeted cell death by non-thermal means comprising the steps of: introducing a particle to the interior of a target cell and exposing the target cell to a transient electric field for a sufficient time interval in order to cause cell death.

Targeted cell lysis is ideally achieved by the steps of: introducing a particle to the interior of a target cell and exposing the target cell to an electric field sufficient to cause irreversible electroporation (IEP) to the cell. However, it is understood that in aspects of the invention some cells may undergo apoptosis as a result of exposure to the electric field.

Preferably the particle is a dielectric particle. Preferably the particle has a high permittivity with respect to the cell and a surrounding environment. In some embodiments the particle comprises a conductive core, such as a metal, for example gold.

As a result of introducing the particle to the interior of the cell, it has been found that when an electric field is applied the particle enhances the effect of the electric field in the vicinity of the particle, so reducing the field strength needed to achieve cell death, for example by electroporation of the cell.

In preferred embodiments the particle is ideally associated with the cell membrane, or in the case of a bacterium, the cell wall. The particle may be adapted to bind or adhere to the cell wall.

As a result of selecting the particle type; its location with respect to the cell; and the specific field characteristics, the cell experiences irreversible pore formation in the cell membrane, at reduced field strength, so causing lysis and cell death at lower than previously achievable electromagnetic field magnitudes, thus reducing the risk of damage to neighbouring cells which do not have particles within them.

Preferably particles are adapted to enter the cell through an outer membrane. It is known in the art that small particles are taken into cells by means of endocytosis and the invention includes the use of particles adapted to this end. Such adaptation may also include providing a surface coating or surface species that promote uptake by cells. Such a coating may include surface molecules such as protein or peptide species known in the art to promote endocytosis. Such coatings may comprise species such as proteins, peptides or nucleic acid species that bind to target molecules on the exterior of the cell membrane, so acting to increase the concentration of particles associated with the membrane, and hence the rate of uptake of the particles by means of endocytosis not specifically caused or enhanced by the coating of the particle.

Advantageously, by positioning a second particle in close proximity with the first dielectric particle, further concentration of the electric field is achieved. A second particle may also be within the cell.

A further way of positioning a second dielectric particle in close proximity with the first particle is to locate the second particle on, or adjacent, an exterior surface of the targeted cell. Upon application of an electric field, local pore forming occurs as a result of the electric field. The effect of this on the target cell is enhanced and this eventually leads to cell death, because the cell quickly loses its ability to sustain its cellular membrane potential and because nutrients leak from the pores. Eventually pore formation becomes irreversible after a few milliseconds of treatment and the cell dies.

When two particles are associated with a cell, in addition to the concentration of electromagnetic field strength, there is also an increase in a mechanical force that is applied to the cell and in some embodiments this may rupture the cellular membrane, (typically of the order of 10 nm thick), for example when particles are positioned on both sides of the membrane, or render it more susceptible to irreversible pore-forming events arising from the field enhancement in the vicinity of the two particles.

According to another aspect of the invention particles may have formed thereon a coating that makes them selective for the target cell type in such a way that at least one particle binds selectively to one or more target molecules in the target cell membrane.

The invention provides means to achieve selective destruction of target cells while non-target cells are left relatively unharmed.

Preferably one or more particles are targeted to target molecules, for example target proteins, that are specifically or preferentially expressed by a target cell type, so promoting the preferential association of particles with the target cell type over non-target cells. Such target molecules may be located on the exterior of the target cell membrane, the interior of the target cell membrane, or at a location within the target cell. Such target molecules may be located preferentially at a specific location or range of locations within the target cell, for example associated with an organelle or interior structure of the target cell, such as, for example, the nuclear or mitochondrial membrane.

The term target molecule means any molecule, or region or fragment of a molecule, for example a protein, present on the exterior or interior of a target cell to which a coating, component or region of a particle may associate or bind. The target molecule may be a biomarker and the terms marker and target molecule are used interchangeably.

Target molecules may be the following or regions or subunits of them: lipid, carbohydrate, a nucleic acid (such as chromosomal DNA and/or plasmid DNA and/or any type of RNA), a protein (for example, from the group comprising: enzymes, structural proteins, transport proteins, ion channels, toxins, hormones, and receptors) or small molecules that can be bound to the cellular membrane either in form of an agonist and/or antagonist compared to its affinity for non-target cells.

In a preferred embodiment, such target cell molecules are located on the exterior of the cell membrane so providing one or more particles bound preferentially to the exterior of the target cell, but not to the exterior of non-target cells. The particles so associated may be adapted to enter the target cell, for example by endocytosis, while particles are not taken up, or are taken up to a lesser extent, by non-target cells.

Such targeting may be achieved by means of antibodies, aptamers or other ligands provided on the surface of the particles. Ligands for known target molecules as described in the prior art may be used in the coating. More than one ligand species may be provided in order to increase the capture affinity.

Such coatings allow the method of the invention to be applied selectively to target cells in a mixed population of target and non-target cells, allowing the field to be chosen so as to cause death of the target cells while leaving the non-target cells unharmed.

Such a coating may be uniform over the surface of the particle or it may be located in a specific region of the particle, for example in the case of an elongated structure, preferentially at one end of the particle or preferentially remote from one end, so allowing the particle to bind preferentially in a preferred orientation with respect to the target cell.

The first particle may be adapted to allow it to enter the target cell by means of endocytosis. Typically the size of the first particle is in the range of 20 nm to 2 um, optionally to 5 um. The second particle may be adapted so as not to promote its uptake by the cells. Typically the size of the second particle is in the range of 20 nm to 5 um.

The first particle optionally comprises a coating adapted to promote endocytosis, or binding to the cell membrane so as to improve the chance of endocytosis. The second particle may have a coating that does not promote endocytosis, or acts to delay or hinder it.

According to another aspect the invention relates to an apparatus for treatment of a disease condition in a subject using particles or nanoparticles and time-varying electromagnetic or electric fields, characterised in that a means is provided to introduce a particle to the interior of a target cell and a means is provided for exposing the target cell to an electric field sufficient to cause cell death by non-thermal means.

Ideally cell death results from irreversible electroporation of the cell. It is understood that in some embodiments cells may undergo apoptosis as a result of exposure to the electric field.

The invention may be used in order to treat for example neoplasia, cancerous cells, or to treat infections caused by fungi, vira, bacteria or other microorganisms.

Ideally the means to introduce particles to the interior of the cell includes a particle delivery device that administers particles to the target cells or a region of tissue comprising them, for example topical or systemic administration. Particles so delivered are preferably adapted to enter the target cell as described above.

Means may be provided as part of the apparatus to provide a first particle type, adapted as described above to enter a target cell, and a second particle type, adapted to bind to a target molecule on the exterior of a target cell membrane. In a preferred embodiment, the first particle type is also targeted to a target cell, as described above, so that it enters a target cell preferentially. In addition entry of the first particle into non-target cells is minimised.

Particles may be administered systemically by, for example, administering into a body fluid such as blood, lymph, cerebrospinal fluid, so that the fluid acts to carry the particles to the target cells. In some embodiments the target cells may be within the body fluid into which the particles are administered. In some embodiments the body fluid may act as a transfer medium to carry, or allow transmission of, the particles to the target cells. The target cells may be bacteria, spores, vira or mammalian cells, for example leukemic or virally-infected cells within the body fluid. The target cells may instead be localised, for example in a local seat of infection, a region of neoplasia or a tumour.

Particles may be administered by any means known in the art, such as injection and/or infusion and/or electroporation through skin and/or inhalation and/or absorption through mucal membranes and/or via the digestive tract.

Devices for administration include: a syringe, cannula, catheter, inhaler, implanted release device, capsule or ingestible preparation.

According to a further aspect of the invention there is provided a means to expose the target cells to a variable electric or electromagnetic field comprising: at least a first and a second electrode and a control means for applying a variable potential to the first and second electrodes, whereby target cells within the electric field are killed and non-target cells remain unharmed. The field strength may be chosen according to the nature of the disease condition, the nature of the particles, and the proportions of target and non-target cells that are to be destroyed on average in a given treatment.

The terms electric and electromagnetic fields are used interchangeably except where stated. The terms electric field, electric field strength and electric field flux are also used interchangeably to refer to the magnitude of an electric field.

The electric field is ideally a time varying field but it will be understood that alternatively, or in addition, the electric field may vary in space, so that a varying field gradient is applied to the targeted cell.

In a preferred embodiment the apparatus comprises: at least a first and second electrode adapted to be located externally to the body of a subject or to be placed in contact with the skin of the subject. It is an advantage of the present invention that the field required for cell death of target cells is sufficiently low that in contrast with the prior art electrodes may be used in some embodiments that do not need to be implanted.

In some embodiments the apparatus may comprise one or more electrodes adapted to be implanted within the body of the subject. In preferred embodiments the electrodes are adapted to provide a field localised in the vicinity of a region of target cells, such as for example a seat of infection or a tumour. In an alternative embodiment the electrodes are adapted to provide a field over a larger region, so as for example to treat a delocalized condition over a region of the subject's body.

In some embodiments the apparatus comprises means to change the orientation of the applied field during a course of treatment. In some embodiments the apparatus includes means to move one or more electrodes with respect to the subject or vice versa.

According to a further aspect of the invention there is provided a method of targeted cell lysis comprising the steps of: causing a particle of high permittivity to associate with the exterior of a target cell membrane and exposing the target cell to an electric field sufficient to cause irreversible electroporation (IEP) to the cell.

In preferred embodiments the particle is a dielectric particle. Preferably the particle has a high permittivity with respect to the cell and a surrounding medium.

In some embodiments the particle comprises a conductive core, such as a metal, for example gold, or a metal oxide, for example $Fe_3O_4$.

Particles are preferably of higher permittivity than the mean permittivity of the composite medium environment in a region surrounding them. Typically that region comprises one or more of the extracellular fluid; extracellular matrix and associated proteins; cell membranes of the target cell and surrounding cells; cell surface molecules such as membrane proteins, glycoproteins and sugars. The permittivity of the surrounding environment is therefore a composite permittivity derived from the presence and permittivities of various composite components, and therefore may take a range of values up to that of physiological saline or blood.

As a result of the particle becoming associated to the cell membrane, or in the case of a bacterium, the cell wall, it has been found that, when an electric field is applied the particle enhances the effect of the electric field in the vicinity of the particle, so reducing the field strength needed to achieve electroporation of the cell.

In preferred embodiments the particle is adapted to bind to a target molecule on the cell membrane as described above. In preferred embodiments the particle is adapted to bind selectively to target cell by means of binding to a target molecule that is preferentially, or only, expressed by a target cell type.

As a result of selecting the particle type to have a high permittivity; its location with respect to the cell; and the specific field characteristics, the target cell experiences irreversible pore formation in the cell membrane at reduced field strength, so causing lysis and cell death at lower than previously achievable electromagnetic field magnitudes, thus reducing the degree of damage to neighbouring non-target cells.

It is additionally found that providing a second particle of high permittivity in close proximity to the first particle, causes a greater enhancement of an applied field than for a single particle alone, or for a pair of particles of low permittivity. Therefore in particularly preferred embodiments first and second high permittivity particles are provided in proximity one to another and to a target cell, an electric field is provided such that death of the target cell is caused by means of damage to a cellular structure or component, for example irreversible electroporation of the cell membrane or the nuclear membrane.

In preferred embodiments the first particle is adapted to enter the target cell and the second particle is adapted to bind to the exterior of the cell membrane as described previously. In an alternative embodiment, both the first and the second particles are adapted to bind to the exterior of the cell membrane.

According to a further aspect, the invention relates to an apparatus for causing targeted cell lysis, comprising: means to provide particles to a target cell, the particles being adapted to associate with the target cell, and means to apply an electric field to a target cell, comprising a first and a second electrode and a device to apply time-varying potentials to the electrodes.

Electrodes and particles may have characteristics as described above. Further characteristics of electrodes and particles that are used in various embodiments of the invention are set out below.

In a preferred embodiment the apparatus comprises a device for providing a time varying first electric potential to the first electrode and second electric potential to the second electrode, and a programmable unit adapted to control the device in response to instructions stored on a storage medium accessible by the programmable unit.

According to a further aspect of the invention there is provided a method for treatment of a disease in a subject by means of destruction of target cells within the subject, comprising the steps of:
a) administering particles to the subject, either systemically or topically in the region of the target cells, the particles being adapted to be taken up within the target cells;
b) allowing a chosen time interval to elapse so that at least one particle is taken up within at least one target cell; and
c) applying an electric field to a region of the subject within which one or more target cells are located in order to cause cell death of the targeted cells by predominantly non-thermal means.

In preferred versions of this embodiment the one or more particles create an enhanced electric field in their vicinity and cause cell death of the target cell by means of irreversible pore forming events in the cell membrane.

The particles may be adapted to be taken up into the target cells. Particles may be adapted to be taken up selectively into target cells, and either not taken up, or taken up to a lesser extent by non-target cells, as described above.

Particles may be administered systemically as described above, or topically by means known in the art such as local injection, infusion, implantation or electroporation.

In a preferred embodiment, a second particle may be provided that is adapted to bind to the exterior of the target cell membrane. One or both particles may comprise a coating that makes them selective for the target cell type in such a way that at least one particle binds selectively to one or more target molecules in the target cell membrane.

Optionally particles may be located and/or tracked within the body fluid or the site of action by means known in the art, for example MRI, ultrasound or computer tomographic (CT) scanner, chosen according to the nature of the particles in use. In addition the electric field may be applied at a chosen point depending on the results from the location and tracking process, and associated processing and display equipment may be provided in order to enable this.

According to a further aspect of the invention there is provided a method for treatment of disease in a subject comprising the steps of: administrating to a subject a quantity of a first particle type, administrating to the subject a quantity of a second particle type; allowing at least one particle of the first particle type and at least one particle of the second particle type to become associated with one or more target cells, and providing an electromagnetic field in the vicinity of the target cells so causing death of the target cells by primarily non-thermal means.

In preferred embodiments the particles become associated with the target cells so as to form an arrangement of particles in which the particles act together to enhance the electric field in their vicinity, so causing damage to a cellular structure, such as the cell membrane or the nuclear membrane, leading to cell death.

In particularly preferred embodiments, the first particle type is adapted to enter the target cell, and the second particle type is adapted to be bound to target molecules on the exterior of the cell. The first and second particles act together to enhance the electric field across the cell membrane in the vicinity of the particles, so causing cell death by means of irreversible pore-forming events.

In preferred embodiments a delay is provided between the administration of the first and the second particle types. The delay is typically in excess of 10 minutes.

In preferred embodiments a delay is provided between administration of the second particle type and application of the electric field. The delay is typically in excess of several minutes, ideally more than 10 minutes.

According to a further aspect of the invention there is provided a method of treatment of disease in a subject by means of targeted cell lysis comprising the steps of: administering a first particle type systemically to the subject, the first particle type being adapted to bind to a target molecule on the target cell membrane; waiting for a time interval to allow the particles to bind to the target cells; and exposing the target cell to an electric field sufficient to cause irreversible electroporation of the cell.

In preferred embodiments the particle is a dielectric particle. Preferably the particle has a high permittivity with respect to the cell and a surrounding medium. In some embodiments the particle comprises a conductive core, such as a metal, for example gold, or a metal oxide, for example $Fe_3O_4$.

In preferred embodiments the particles are adapted to bind to target molecules on the exterior of the cell membrane, and preferably comprise a coating as described previously.

According to another aspect the invention relates to an apparatus and a method for treatment of a disease condition in a subject using particles or nanoparticles and time-varying electromagnetic or electric fields, characterised in that a means is provided to associate a particle selectively with a target cell in a liquid medium and a means is provided for exposing the target cell to an electric field sufficient to cause irreversible electroporation of the cell.

Preferably treatment of a disease in a subject by causing death of target cells located at least partially in a body fluid comprises the steps of: administering particles to the body fluid, allowing the particles to become associated with target cells within the body fluid, applying an electric or electromagnetic field to the target cells and particles within the body fluid, thereby causing cell death by primarily non-thermal means, for example by irreversible electroporation of the target cell membrane.

An example of a body fluid may be blood or a blood component such as plasma, cerebrospinal fluid, or bone marrow. Optionally treatment of the body fluid is performed on the fluid after it has been removed from the human or animal body or is performed whilst the fluid is outside the human or animal body.

In a preferred embodiment an apparatus comprises particles adapted to bind to a target molecule on the surface of a target cell, or to enter a target cell, as described previously; means to administer particles into the body fluid; at least a first and a second electrode adapted to apply an electric field to a region of body fluid containing target cells and a device for providing time varying potentials to the first and the second electrodes.

Preferably the electrodes apply an electric field to a region through which a body fluid flows, so bringing target cells into the region with the flow. In an embodiment the electrodes are adapted to apply a field to a perfused region such as a blood vessel in vivo, for example a blood vessel near the surface of the body.

In an alternative embodiment the apparatus includes means for applying an electric field to a body fluid externally to the body. Preferably the apparatus comprises an extracorporeal flow system comprising a flow cell through which the body fluid, such as blood, may flow, the flow cell being adapted to apply an electric field to the fluid. The flow system may then return the treated fluid to the subject.

The method according to this aspect of the invention preferably includes steps of: administering particles systemically to the subject, allowing a time interval after administration, and then providing an electric field in a region containing the body fluid or through which the body fluid may flow. The method preferably includes a repeated application of the field in order to cause death of the target cells as they move into a region where the electric field is applied. The method envisages that target cells may be delocalized within the body fluid of the subject, and present at low concentrations within the body fluid, so may be removed gradually by repeated applications of the field over time. It is a feature of the invention that the reduction in field strength and electrode potentials needed to achieve irreversible electroporation and cell death facilitates repeated applications of the field compared with prior art apparatus and methods.

The terms lysis, cell death, cell destruction and killing are used interchangeably.

For the avoidance of doubt the term subject is meant to include a living organism including individual humans and animals. The terms subject, host organism and target organism are used interchangeably.

The mechanism of cell destruction according to the invention is described as irreversible electroporation, or irreversible pore-forming event, those terms are used interchangeably. It is further understood that in embodiments of the invention cell death may occur through exposure to transient electric fields enhanced by particles without irreversible electroporation of the cell membrane, rather through damage to intracellular structures, organelles or components leading to apoptosis or necrosis.

It is further understood that features described for given aspects of the invention or embodiments are not intended to be employed in that aspect or embodiment only, rather they may be combined to achieve the purposes of the invention.

In some embodiments particles may be adapted to remain associated with target cells for an extended period after administration. Thus in accordance with any of the aspects of the invention herein, the method may comprise administration of particles followed by multiple instances of application of the electric field at intervals after administration of the particles.

According to a further aspect of the invention there is provided a method for causing the death of a target cell, comprising the steps of: providing a particle arrangement of at least a first and a second particle in proximity to the target cell; applying an electric or electromagnetic, field to the target cell and particle arrangement, the first and the second particles being arranged such that they cause enhancement of the component of the field appearing across a region of the target cell in the vicinity of the first and second particles, so causing cell death by primarily non-thermal means.

In a preferred embodiment the first and the second particle are arranged so that a region or component of the target cell lies between them.

Preferably the first and the second particle are located on opposite sides of the target cell, of an organelle within the target cell, for example the nucleus, or of a cell component, for example the cell membrane, the nuclear membrane or a mitochondrial membrane, in the direction of a component of the applied electric field, thereby enhancing the applied field appearing across the cell, organelle or component. A field may then be applied so as to cause disruption of the cell, organelle or component, leading to cell death. Cell death may be caused for example by irreversible electroporation of a membrane.

In a preferred embodiment sufficient particles are provided such that on average a proportion of target cells have a particle arrangement as above. The number of particles supplied and the applied field strength may be chosen to optimize the proportion of target and non-target cells destroyed by the field.

The electric field may be applied in a first direction and then subsequently in a different orientation, for example by moving one or more electrodes used to provide the field relative to the cell. As described further below, a plurality of electrodes may be provided to allow the field direction to be chosen or varied during the treatment.

A further aspect of the invention provides a method for selectively killing a cell, the method comprising the steps of: providing a particle arrangement of at least a first and a second dielectric particle, where the first dielectric particle is within the cytoplasma of the cell and the second dielectric particle is on the extracellular side of cell.

An alternative approach is where both the first and second dielectric particle is at the extracellular side of the cell or both particles are in the cytoplasma of the cell. However, both alternatives are likely to give lesser effect than the first mentioned arrangement.

Ideally a coating is provided on at least one of the particles so as to render it specific for the target cell type in such a way that at least one particle binds selectively to one or more target molecules in the cellular membrane.

Optionally by providing at least a first and a second electrode externally to the organism hosting the target cell.

Additionally the particles are exposed to an alternating electric field, the alternating electric field being provided by at least the first and the second electrodes and being of sufficient frequency and amplitude so as to cause a concentration of field flux between the at least two particles so as to cause destruction of molecular entities in the target cell.

This ultimately leads to break down of the cellular membrane by causing irreversible pore forming events. The field amplitude and frequency can be chosen so that cellular destruction is achieved in the vicinity of the two dielectric particles and so that adjacent cells are unaffected, because it is only the field flux concentration between the two dielectric particles that is strong enough to mediate molecular disarrangement for example in the cellular membrane.

Preferred embodiments of this and other aspects of the present invention may comprise some or all of the following features.

In a preferred embodiment of the invention, the method may further include the step of performing an analysis of the extent of cellular damage, said step comprising extracting biological material from the host organism and subjecting extracted material to an investigation in order to determine the damage. Alternatively, the analysis may involve a non-invasive technique such as ultrasonic investigation, computer tomography (CT), X-ray or magnetic resonance image analysis.

The terms "killing" relate to cause irreversible pore forming events in the cellular membrane or in case of bacteria the cell wall, with concomitant release of biological material from the target cells. In the present context the term "target cell" is related to a biological form of life comprising for example, a microorganism, a virus, or an eukaryote cell.

In a preferred embodiment of the invention, the microorganism is hosted inside a mammalian cell which is serving as a reservoir for the infection.

In a preferred embodiment of the invention, the microorganism is resistant to common chemotherapies such as anti-biotics such as but not limited to methicillin-resistant *Staphylococcus aureus* (MRSA), vancomycin-resistant *Staphylococcus aureus* (VRSA), penicillin resistant *Streptococcus*, anti-biotic resistant strains of *Mycobacterium tuberculosis*, penicillin resistant *Enterococcus*, multi-drug resistant *Pseudomonas aeruginosa*, clindamycin (or fluoroquinolone) resistant *Clostridium difficile* (diarrhea) disease) and multi-drug resistant *Escherichia coli*.

In an embodiment of the invention, the first and a second electrode are separated by a distance being at the most 1 m, preferably being at the most 0.9 m, such as at most 0.8 m, 0.7 m, 0.6 m, 0.5 m, 0.4 m, 0.3 m, 0.2 m, 0.1 m, or at most 0.05 m, more preferably being at the most 0.04 m, and even more preferably at most 0.03 m such as at most 0.02 m, such as at most 0.01 cm.

For example the first and the second electrode may be separated by a distance in the range of 0.01-1 m, such as in the range of 0.01-0.05 m, 0.05-0.1 m, 0.1-0.2 m, 0.2-0.3 m, 0.3-0.4 m, 0.4-0.5 m, 0.5-0.6 m, 0.6-0.7 m, 0.7-0.8 m, 0.8-0.9 m or such as in the range of 0.9-1.0 mm.

Typically, the first and the second electrode are separated by a distance, which is at least 0.01 m such as at least 0.03 m or 0.05 m.

Normally, at least a part of the target cells in the organism is positioned between the first and the second electrode. For example, at least 1% of the target cells are positioned between the first and the second electrode, such as at least 5, 10, 20, 30, 40, 50, 60, 70, 80, 90, 95, 97.5, 99, 99.5, 99.9 or 100% of the 1% of target cells are destroyed by the electrical field imposed by the first and the second electrode.

Preferably, in use, the target cells located in the organism are positioned between at least the first and the second electrode as part of the method. The first or the second electrode may be attached directly to surface of the organism.

The first and/or the second electrode may have different shapes or dimensions. For example, the first and/or the second electrode may have a substantial form chosen from the group of a sheet, a plate, a disc, a wire, a rod; or any combination thereof.

In a preferred embodiment of the present invention, the first and the second electrode may for example be a combination of a point electrode and a sheet electrode.

In a preferred embodiment of the present invention the first electrode and the second electrode are facing each other. For example, they may be positioned at opposite sides of the organism hosting the target cells creating a field that is optimal for concentrating the electric field flux between the two particles.

The first and second electrodes may take any appropriate form as described in the art. The present invention offers the advantage that the field needed for successful killing of target cells is lower than in the prior art, so allowing a wider range of electrode types and locations during treatment to be used.

In a preferred embodiment relating to treatment of disease in a subject one or both of the first and second electrodes are implanted within the body of the subject (i.e. the organism hosting the target cells). One or both of the first and second electrodes may be implanted in the vicinity of a group of target cells, such as a tumour.

An implanted electrode may be positioned within, adjacent to or around the group of target cells. In an embodiment one or both of the first and second electrode may take the form of a probe that may be manipulated by a clinician to apply an electric field locally to the probe, so allowing the clinician to position the electrode in order to apply the field to a chosen region. The probe may be adaptable to be used during a surgical procedure that exposes a deep-seated group of target cells, for example a tumour, the probe then being applied to a chosen area by the clinician.

The first and second electrodes may both take the form of probes, and both might be usable in this way. Alternatively the second electrode may be adapted to remain in a fixed location while the first is moved. In some embodiments the second electrode may have an extended conducting surface, for example in contact with soft tissue of the subject, and may in some embodiments be in contact with the skin of the subject.

In some embodiments the electric field may be applied in a single orientation between the first and second electrodes. In further embodiments the electric field may be applied in further orientations relative to the target cells or to an organism that hosts the target cells, such as in the case of treatment of disease in a subject. This may be achieved in some embodiments by changing the disposition of one or more electrodes relative to each other or to the subject, for example by moving either one or more electrodes or moving the subject. In further embodiments more than two electrodes may be provided in order to allow the field to be applied in a number of different orientations.

The potential difference between the first and second electrode may be in a range that causes an electric field flux concentration between the said first and second particles to generate molecular rearrangements associated with cellular destruction as e.g. the pore forming events described previously.

An electrode, for example a first electrode in a pair of electrodes, may be formed from a variety of different materials. Optionally the first electrode and a second electrode are formed from the same material. Typically, the electrodes are formed from metals or alloys. The first and the second electrode may for example comprise a metal selected from the group comprising: silver, gold, platinum, copper, carbon, iron, graphite, chromium, nickel, cobalt, titanium, mercury or an alloy thereof.

It is also envisaged that an electrode may comprise a conducting liquid and even essentially consist of a conducting liquid. The conducting liquid may e.g. be mercury.

In preferred embodiments, a typical dimension of the particles is less than 0.1 micrometer (µm).

The core of embedded particles can be formed from a range of materials capable of behaving as a dielectric such as but not excluded to carbon, iron oxide (various forms), titanium dioxide, cerium oxide or silicon dioxide.

In other preferred embodiments the particles may be in the form of nanoparticles which may take the specific form of nanotubes. Alternatively the particles may be substantially spherical, for example cubic or octahedral, or they may be nanorods.

The dimension or/and structure of electrodes typically depends on the dimension of an optimal target area of a host organism.

Advantageously the length and width of the electrodes are of the same order of magnitude as the radius of a target area on the target cell.

The electrodes can be formed by as little as a coating of a few atom layers of conductive material.

In an embodiment a first and/or second electrode has a thickness in the range of 0.001 µm-2000 µm, such as 0.001 µm-1 µm, 1 µm-20 µm, 20 µm-200 µm, and 200 µm-2000 µm.

In use, a liquid sample, in which cells are supported, is exposed to an alternating electric field, which is provided by the first and the second electrode. It is important that the alternating electric field has a sufficient frequency and sufficient amplitude and is applied for a sufficient duration of time to cause necessary molecular destruction of the target cell so as to cause selected killing of the target cell whereas non-target cells remain relatively unharmed.

The term alternating electric field relates to electric fields that change over time. The alternating electric field may e.g. be the electric field that occurs from periodically shifting the polarity of two electrodes between positive/negative and negative/positive, that is connecting an AC source to the electrodes. Also, the alternating electric field may comprise one or more DC pulses.

Pulses may have a duration in the range 1 ns to 100 ms, preferably in the range 10 ns to 1 ms. Pulses may generally have durations and repetition rates, patterns and numbers of pulses as known in the practice of electroporation, in particular for irreversible electroporation, the use of particles in accordance with the invention increasing the effect of each pulse or train of pulses. Ultrashort pulses in the range 1-100 ns may be used as known to result in apoptosis without irreversible electroporation of the cell membrane.

In a preferred embodiment of the invention, the frequency of the alternating electric field is at the least 10 kHz, preferably being at least 50 kHz, and more preferably being at least 100 kHz.

In another preferred embodiment of the invention, the frequency of the alternating electric field is at the least 100 kHz, preferably being at least 500 kHz, and more preferably being at least 1000 kHz.

In another preferred embodiment of the invention, the frequency of the alternating electric field is at the least 1 MHz, preferably being at least 50 MHz, and more preferably being at least 100 MHz.

In another preferred embodiment of the invention, the frequency of the alternating electric field is at the least 100 MHz, preferably being at least 500 MHz, and more preferably being at least 1 GHz.

In another preferred embodiment of the invention, the frequency of the alternating electric field is at the least 1 GHz, preferably being at least 500 GHz, and more preferably being at least 1 THz.

For example, the frequency of the alternating electric field may be at least 10 kHz, such as at least 30 KHz, 100 KHz, 300 KHz, 1 MHz, 10 MHz, 30 MHz, 100 MHz, 300 MHz, 1 GHz, 10 GHz, 30 GHz, 100 GHz, 300 GHz, such as at least 1000 GHz.

Preferably the frequency of the alternating electric field is at most 500 GHz, such as at most 1000 GHz.

The amplitude of the alternating electric field, that is, the maximum potential difference between the first and the second electrode, is typically at most 100 KV, such as at most 30 KV, 10 KV, 1 KV, 300V, 100V, 30V, 10V such as at most 1 V.

The cellular destruction of the said target cells in the host organism is strongly dependent on the design of, and the distance between, the first and the second electrode, the electrode structure and the materials of at least first and second particles located within and in proximity of the extracellular side of the cell membrane or cell wall (bacteria) and the potentials and frequencies applied to the first and the second electrode.

In a highly preferred embodiment of the invention, the first potential of the first electrode and the second potential of the second electrode, and thus the alternating electric field between the first and the second electrode, are modulated so as to yield a cellular destruction of target cells in a target area of at least 30% of the target cells, such that at least 40% of the target cells, preferably of at least 50% of the target cells, and more preferably of at least 60% of the target cells, such as of at least 70%, 80%, 90%, 95%, 97.5%, 99%, 99.5% or 99.9% such as approximately of 100% of the target cells are destroyed.

In another highly preferred embodiment of the invention, the first potential of the first electrode and the second potential of the second electrode, and thus the alternating electric field between the first and the second electrode, are modulated so as to yield a specific cellular destruction of target cells in a target area and survival of at least 70% of the non-target cells, such that at least 75% of the non-target cells, preferably of at least 80% of the non-target cells, and more preferably of at least 85% of the non-target cells, such as of at least 90%, 95%, 97.5%, 99%, 99.5% or 99.9% such as approximately of 100% of the non-target cells survives the treatment.

In another highly preferred embodiment of the invention, the first dielectric particle and the second dielectric particle can mediate a field flux concentration compared to of the potential supplied by the first and the second electrode, so that the field flux concentration between said particles, existing in an area between the two particles, is at the least a factor 1.1, preferably being at least a factor 10, and more preferably being at least a factor 100 compared to the surrounding field flux.

In another highly preferred embodiment of the invention, the first dielectric particle and the second dielectric particle are loaded in the extracellular fluid of the target organism e.g. for humans that means the blood stream, in a time separated sequential manner so that the first particle has time to accumulate in the cytosol of the target cells before the second particle is loaded for binding to the extracellular side of the cellular membrane or cell wall (bacteria).

In an embodiment of the invention, the loading in the extracellular fluid of the first and a second particles, are separated in time by an interval being at the most 30 days, preferably being at the most 20 days, such as at most 10 days, 9 days, 8 days, 7 days, 6 days, 5 days, 4 days, 3 days, 2 days, 1 day, 18 hours, 16 hours, 14 hours, 12 hours, 10 hours, 8 hours, 6 hours, 4 hours, or at most 2 hours, more preferably being at the most 1 hour, and even more preferably at most 30 minute such as at most 20 minute, such as at most 10 minutes.

Typically, the alternating electric field is provided by modulating the polarity of the two electrodes.

The alternating electric field may have a substantial form chosen from the group consisting of: rectangular, sinusoidal, saw-tooth, asymmetrical triangular, symmetric triangular; or any combination thereof.

Also, the alternating electric field, in the frequency domain, may comprise at least a first and a second frequency component.

In an embodiment of the invention, the duration of which the organism is exposed to the alternating electric field is at most 3600 seconds, such as at most 3000, 2000, 1000, 500, 250, 100, 50, 40, 30, 20, 10, 5, 4, or 3 seconds, such as at most 1 second.

For example, the duration of which the organism is exposed to the alternating electric field is in the range of 0.01-3600 seconds, such as in the range of 0.1-1, 1-5, 5-10, 10-25, 25-50, 50-100, 100-250, 250-500, 500-1000, or 1000-2000 seconds, such as in the range of 2000-3600 seconds. In a preferred embodiment of the invention, the duration of which the organism is exposed to the alternating electric field is in the range of 5-100 seconds, such as 6-90 seconds, 7-80 seconds, 8-70 seconds, 9-60 seconds and 10-50 seconds.

In a preferred embodiment of the invention, the organism is exposed to the alternating electric field for at most 250 second, preferably for at most 100 second such as for at most 30 seconds.

The particles are to be coated with a composition that will enhance the binding to target cells over non-target cells in the host organism. In preferred embodiments the coating comprises at least one molecular component that increases the affinity of the particle for a target cell membrane, organelle, lipid, carbohydrate, a nucleic acid (such as chromosomal DNA and/or plasmid DNA and/or any type of RNA), a protein (e,g, from the group comprising enzymes, structural proteins, transport proteins, ion channels, toxins, hormones, and receptors) or small molecule that can be bound to the cellular membrane either in form of an agonist and/or antagonist compared to its affinity for non-target cells.

Another aspect of the invention relates to a device for selectively killing of target cells in an organism, the device comprising: a set of electrodes to be functionally associated with the device, an electrical interface between the device and the electrode arrangement for applying an alternating electric field between the electrodes, an electronic circuit capable of providing a fast switching high amplitude signal and a programmable unit.

The programmable unit ideally contains instructions, preferably computer readable such as software, adapted to facilitate controlling, monitoring, and/or manipulating of the device prior to operation, under operation, and/or after operation.

The programmable unit preferably comprises at least one computer having one or more computer programs stored within data storage means associated therewith, the computer system being adapted to control a system employing first and second electrodes arranged to apply an alternating electric field.

The programmable unit may in the context of the present invention be chosen from the non-exhaustive group of: a general purpose computer, a personal computer (PC), a programmable logic control (PLC) unit, a soft programmable logic control (soft-PLC) unit, a hard programmable logic control (hard-PLC) unit, an industrial personal computer, or a dedicated microprocessor.

The present invention also relates to a computer program product, such as one recorded on a data storage medium, being adapted to enable a computer system, comprising at least one computer having data storage means associated therewith to control, monitor, and/or manipulate the device prior to operation, under operation, and/or after operation.

Advantageously a computer readable medium has stored thereon a set of routines for enabling a computer system comprising at least one computer having data storage means associated therewith to control, monitor, and/or manipulate the device prior to operation, under operation, and/or after operation. The programmable unit is ideally capable of: checking that electrodes are functionally associated with the device, providing a voltage protocol to the electrodes, and setting total time, amplitude and frequency of the applied signal. Secondly being able to repeat the voltage protocol in a number of series with a given time interval between each exposure.

Optionally target cells are exposed whilst in a host organism to an alternating electric field via the electrode arrangement, said alternating electric field being provided by the first and the second electrode and having a sufficient frequency and a sufficient amplitude so as to cause the selective killing of the target cells in the host organism, and optionally performing an analysis on the exposed organism which part comprises an analysis of the damage to target and non-target cells in the affected area of the host organism.

The device may further comprise an electrical power supply for supplying the high voltage needed for the first and second electrodes to achieve the needed effect on the said first and second particle.

In an embodiment of the invention, the programmable unit comprising the software furthermore ensures that the device checks that electrodes are functionally associated with the device.

According to a further aspect the invention provides a composition comprising: a plurality of particles adapted for use in a method and system for causing the death of a target cell by primarily non-thermal means, for example by irreversible electroporation, the particles being adapted to associate with the target cells and adapted to cause an enhancement of an applied electric or electromagnetic field in their vicinity.

In various embodiments the particles have properties as described herein. The composition of the invention may comprise further components to maintain the efficacy and useful life of the composition, for example to maintain the particles in suspension, to aid their administration to a subject, to aid their circulation within the body fluid of a subject for example in the blood, or to aid their absorption into the soft tissue of a subject.

According to a further aspect of the invention a system is provided for the causing the death of a target cell comprising: at least a first composition as described herein, comprising a plurality of at least a first particle type, the particle being adapted to associate with the target cell and adapted to cause an enhancement of an applied electric or electromagnetic field in its vicinity; and an apparatus for applying an electric field to one or more target cells and to one or more particles associated with the target cells, comprising at least a first and a second electrode and a device for providing a first electric potential to the first electrode and a second electric potential to the second electrode, the device comprising a programmable unit adapted to control the device in response to instructions associated with the programmable unit.

A method as disclosed herein, carried out using the composition and the apparatus.

In a preferred embodiment the system may additionally comprise: a second composition comprising at least a second particle type, the second particle type being adapted to associate with the target cell and adapted to cause an enhancement of an applied electric or electromagnetic field in its vicinity. The second particle type may have any of the properties as described herein.

In various embodiments the particles have properties as described herein. In preferred embodiments at least one particle type comprises a coating that makes it selective for the target cell type in such a way that at least one particle will bind selectively to one or more target molecules in the cellular membrane.

According to a further aspect of the invention a system is provided for treating a disease in a subject comprising the composition, apparatus and method as listed above.

In a preferred embodiment the system may additionally comprise a second composition, comprising at least a second particle type, the second particle type being adapted to associate with the target cell and adapted to cause an enhancement of an applied electric or electromagnetic field in its vicinity. The second particle type may have any of the properties as described herein.

In a further embodiment the system additionally comprises: means for administering the composition to the subject, the administration being topical i.e. in the vicinity of the target cells, systemic, or both, said means being for example (but not being limited to): a syringe, a cannula, a catheter, an inhaler, an implanted release device, a capsule or ingestible preparation or means for administration using electroporation. A first means for administration may be used with the first composition and a second means for administration may be used with a second composition.

According to a further aspect of the invention there is provided an apparatus and a method for a biological process, the method comprising the steps of: providing a number of at least a first particle type to cells in culture, the cells comprising target cells, the particles adapted to associate selectively with target cells; allowing the particles either to bind to target molecules on the surface of the target cells or to be taken up inside the target cells; and applying an electric field to the cells in culture, so causing death of target cells by primarily non-thermal means, for example by irreversible electroporation of the cell membrane.

In a preferred embodiment the cell is contained within a liquid media, the particles are mixed with the media and the field is provided within the media by electrodes either within the media or external to it. The electrodes may be insulated from the media. There may be an air gap between the electrode surface and the media.

Preferably the method comprises provision of first and second particle types as described previously.

In a preferred embodiment the apparatus may comprise: particles of at least a first particle type, and optionally particles of a second particle type; a culture container adapted to allow the provision of an electric field to the cells in culture, and at least a first and a second electrode adapted to provide a field to the culture container. In an alternative embodiment, the apparatus may comprise a flow system having a flow cell through which cells may flow in a liquid medium, the flow cell being adapted to provide an electric field to the flowing cells, such that target cells are destroyed selectively.

According to a further aspect of the invention there is provided an apparatus and a method for an analytical process, the method comprising the steps of: providing a plurality of a first particle type to cells in a liquid sample; allowing the particles either to bind to target molecules on the surface of the cells or to be taken up inside the cells; and applying an electric field to the liquid sample, so causing lysis of cells by irreversible electroporation of the cell membrane.

This aspect relates to analytical or diagnostic processes in which it is desired to release cell contents into a liquid sample, for example in analysis of DNA, RNA, proteins or other constituents of the cell. The method of the invention provides a ready means for lysis of cells at low electric fields and hence with lower electrode potentials than in the prior art. The particles may be taken up into the cells or be associated with the external surface of the cell membrane.

In a preferred embodiment the particles are selective for target cells by binding selectively to target molecules on the target cell membrane as described previously, so enabling selective lysis of target cells while non-target cells remain intact. In a preferred embodiment a first particle type is taken into the cell and a second particle type is bound to the exterior of the cell membrane, so reducing the threshold field for irreversible electroporation.

In a preferred embodiment an apparatus comprises particles adapted according to the invention; means to add particles to a liquid sample and means to apply an electric field to the sample. The apparatus may comprise a flow system having a flow cell within which the liquid sample may be exposed to an electric field.

According to a further aspect the invention provides a method for enhancing an applied electric field in a region of a cell, comprising: providing at least one particle to the cell, the particle having a high permittivity or conductive core and being adapted to associate with the cell; and applying an electric field to the cell.

Preferably the said at least one particle is adapted as described herein. Preferably at least two particles are provided to a cell, the particles being adapted to act together to enhance the electric field in their vicinity. In preferred embodiments a first particle adapted to enter the cell is provided, and a second particle adapted to bind to a target molecule on the exterior of the cell membrane is then provided, so as to provide an arrangement of a first particle on the inside of the cell membrane and a second particle external to the cell membrane, in proximity to the first, so causing enhancement of the applied field across a portion of the cell membrane.

The present invention will now be described, by way of examples only, and with reference to the Figures in which:

BRIEF DESCRIPTION OF THE FIGURES

FIG. 7a is a diagrammatical view of a single particle inside a cell;

FIG. 7b is a diagrammatical view of a single particle inside a cell away from the membrane, concentrating the field in a region adjacent the cell membrane;

FIG. 7c is a diagrammatical view of a particle inside a cell and adjacent (or in contact with) the cell membrane, concentrating the field effectively at the cell membrane;

FIG. 7d is a diagrammatical view of a particle bound to a target molecule on the inside of the cell membrane;

DETAILED DESCRIPTION OF PREFERRED EMBODIMENTS OF THE INVENTION

In the following description the terms particle, microparticle, microsized particle and nanoparticle are used interchangeably.

Appropriate dimensions and morphology of particles are described by way of example only.

Example 1

The Effects of Varying Bead Concentration (2, 0.5 and 0 µl) on Spore Electrolysis Efficiency One hundred mg of Biobit *Bacillus thuringiensis* subsp. *kurstaki* containing $3.2 \times 10^9$ spores/g (Valent BioSciences Corp, Libertyville, USA) was resuspended in 1 ml of demineralized water and centrifuged for 90 sec. at 12000 rpm. This procedure was repeated 4 times. The supernatant was discarded. The final solution contains approximately $3.2 \times 10^8$ spores. This solution was diluted to a final concentration of $3.2 \times 10^5$ spores/ml. and subsequently 12 µl spore sample was used for electrolysis and PCR.

Figure 1:
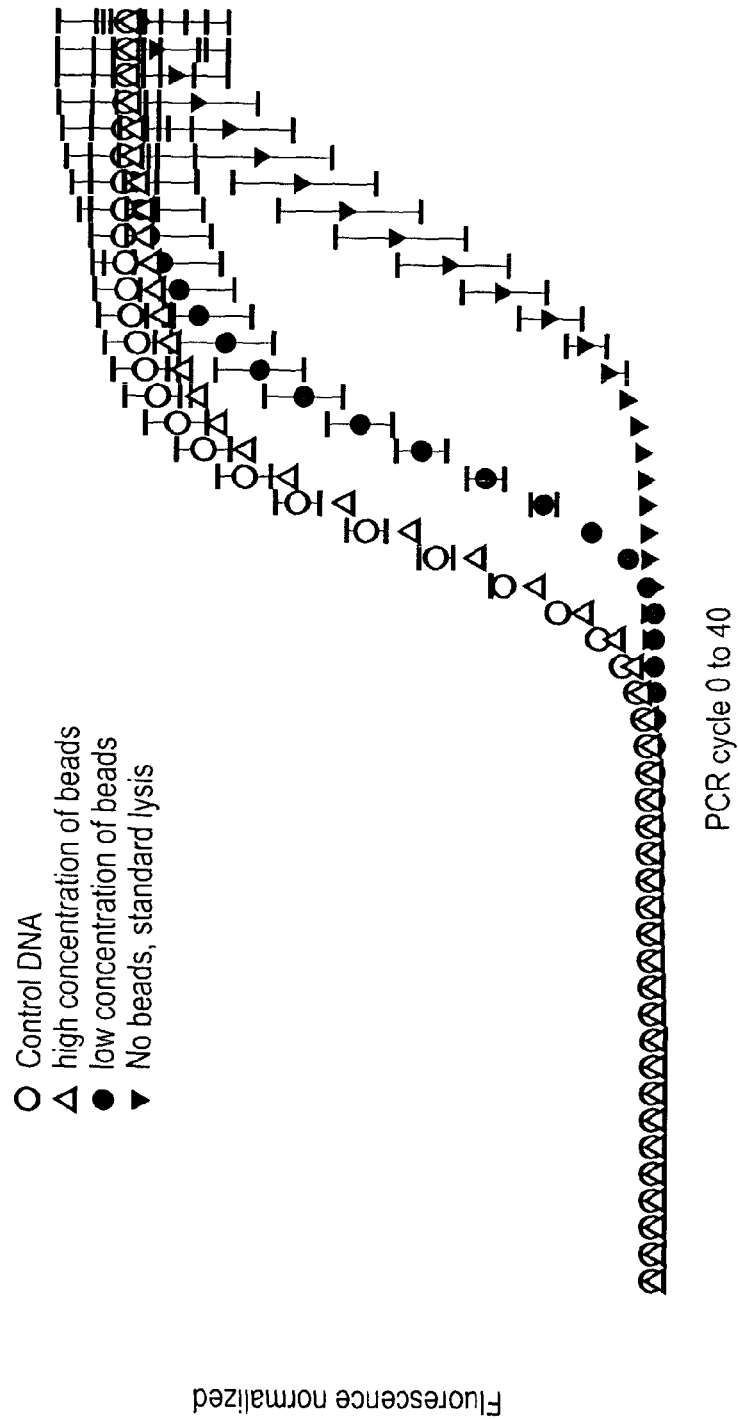
FIG. 1 shows a plot illustrating the effect of the said method on bacterial spores. The effect is monitored as the release of DNA due to electrolysis.
Figure 2:
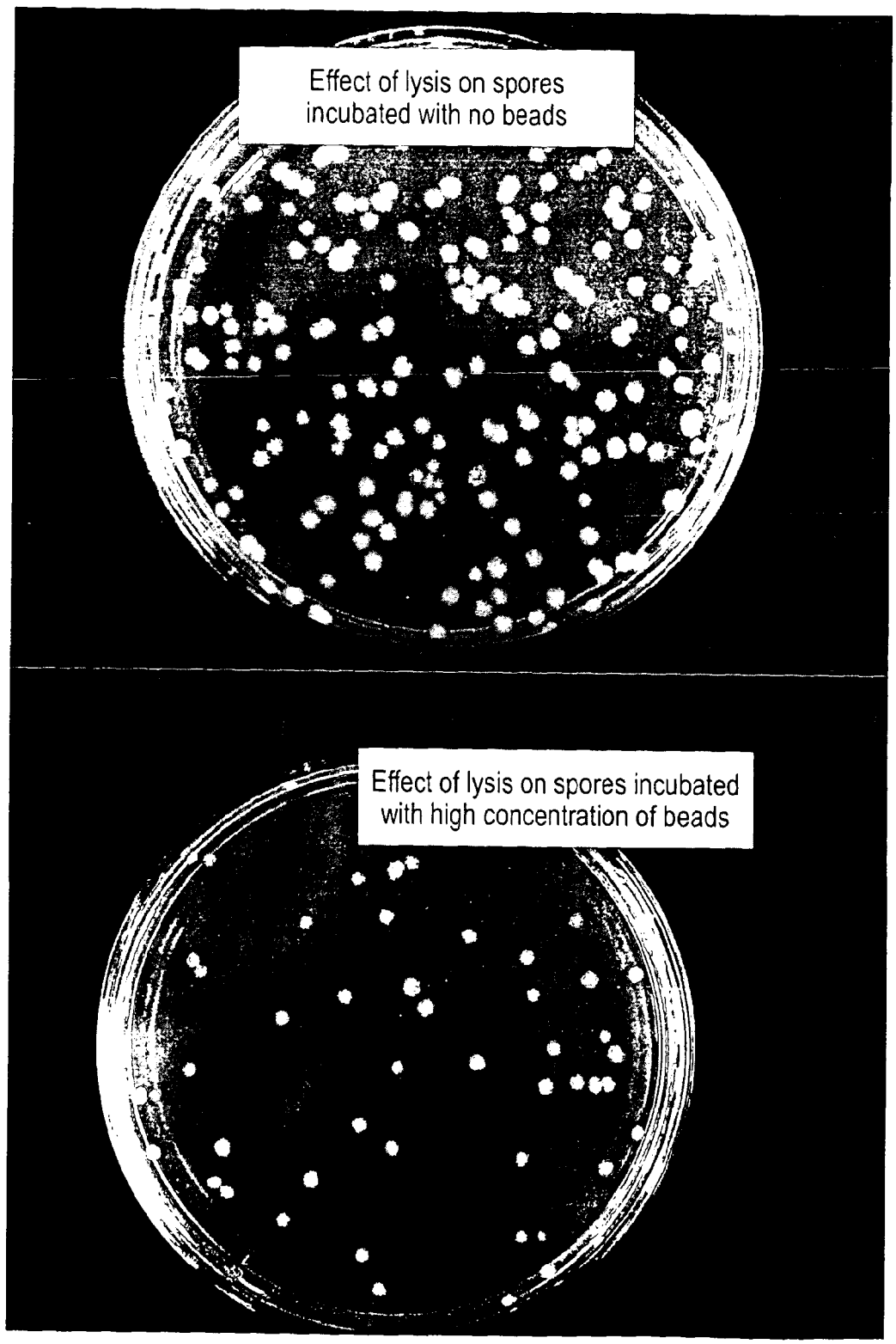
FIG. 2 shows a plot of colony forming unit (CFU) of two populations of bacterial spores where one has been exposed to the method and the other has not (control)

Voltage, time and frequency were kept constant (at 10 V, 30 sec and 100 KHz, respectively) variations was made in the concentration of iron oxide beads that was added respectively 2 and 0.5 µl 1 µM iron oxide silica coated beads (Merck). FIG. 2 shows the results of this experiment and as apparent, the high concentration of bead of 2 µl to the 12 µl spore sample showed a decrease in $C_T$ (threshold cycle) compared to standard lysis without beads, thus demonstrating release of amplifiable DNA from the spores. Lowering the bead concentration to 0.5 µl decreased the effect considerably.

It other experiments it was shown that addition of more than 0.5 µl silica coated iron oxide beads directly to a 20 µl PCR reaction gave more than 50% in the PCR yield. The above experiments was carried out with a final bead addition of respectively $1/12 \times 2 = 0.17$ µl bead to a 20 µl PCR reaction for the high concentration of beads and a $1/12 \times 0.5 = 0.04$ µl bead to a 20 µl PCR reaction for the low concentration of beads. Therefore, it should be expected that less PCR inhibition is experienced in the low concentration of bead than in the high concentration. The results are opposite that, thus the effect of the increased beads is exceeding the PCR inhibition.

It is believed that the effect of the increased bead concentration is to increase the likelihood of forming two particle arrangements on opposing sides of the spore leading to an increased field flux between the particles with concomitant molecular disarrangements in the coating of the spores and cell wall leading to killing of the spore.

FIG. 2 shows the spores grown on agar plates subsequent to the lysis and spores incubated with beads and grown show no effect whereas the number of colony forming units from the sample undergone the electrolysis in presence of beads shows a marked reduction (95% less CFU's compared to control).

Figure 3:
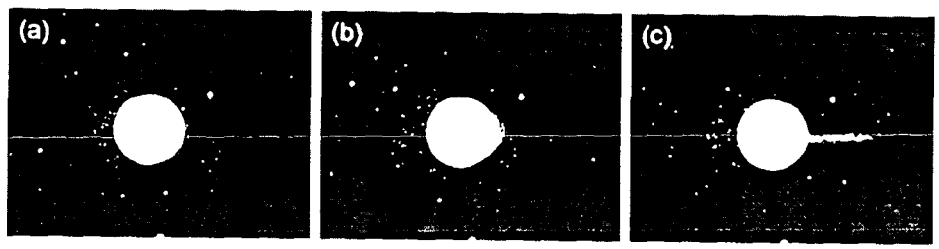
FIG. 3 shows the time course of pores formed in a cellular membrane.
Figure 3:
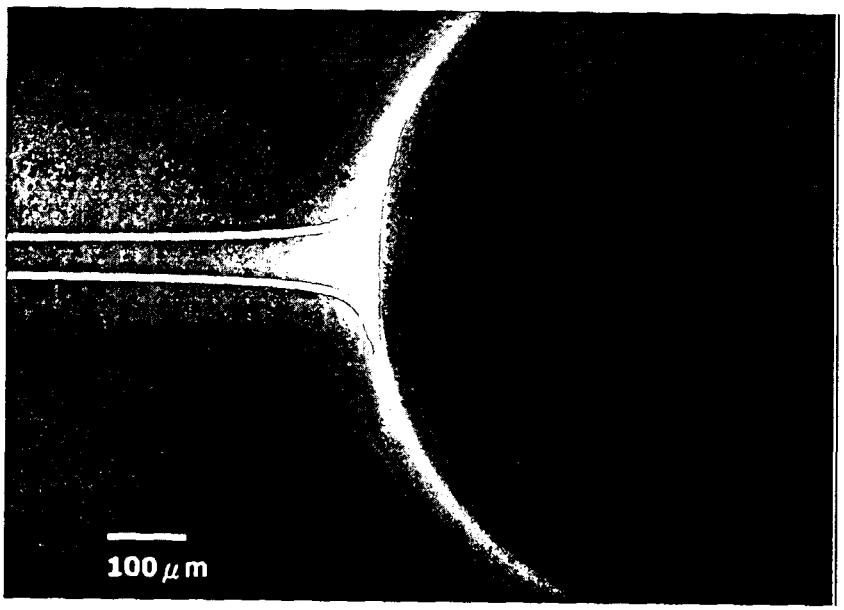

FIG. 3 illustrates the field flux from a sphere formed particle in a non-homogenous electrical field. The field flux increase causes fluorescent ions to move in the most concentrated region of the flux and electromotion overcomes diffusion and a concentrated stream of fluorescent ions is radiating out from the sphere. The same principles are governing smaller particles and can be used to generate a electric flux concentration between two particles with associated molecular rearrangement for any charged molecule within the concentrated flux region.

A) The sequential images of microparticle concentration evolution for a cation exchange granule with a step change in the field to 100 V/cm, using co-ion fluorescein-dye tagged microspheres in 10 mM Tris buffer (pH 8) at very low density (5.0×10E6 particles/mL). The images are taken at 0 (a), 1.35 (b), and 2.44 s (c).

B) Ion-concentrated ejection cone. The yellow profile is the theoretical prediction of:

$$R/a = (\sqrt{3}/\Gamma \, 0.75)(1-(a-r)_3)-0.5,$$

based on flux balance within the two bounding pole field lines.

R: radius of jet ejecting from the sphere r: radius of sphere a: area of sphere

Γ field in volt per cm

This principle is also governing smaller particles and can be used to create a electric flux concentration between two particles with subsequent molecular disarrangement of charged molecules between the two particles. In the case of a cell membrane intercalated between the two particles it will lead to pore forming events in the cellular membrane. (Biomicrofluidics 2008, 2, 014102)

Figure 4:
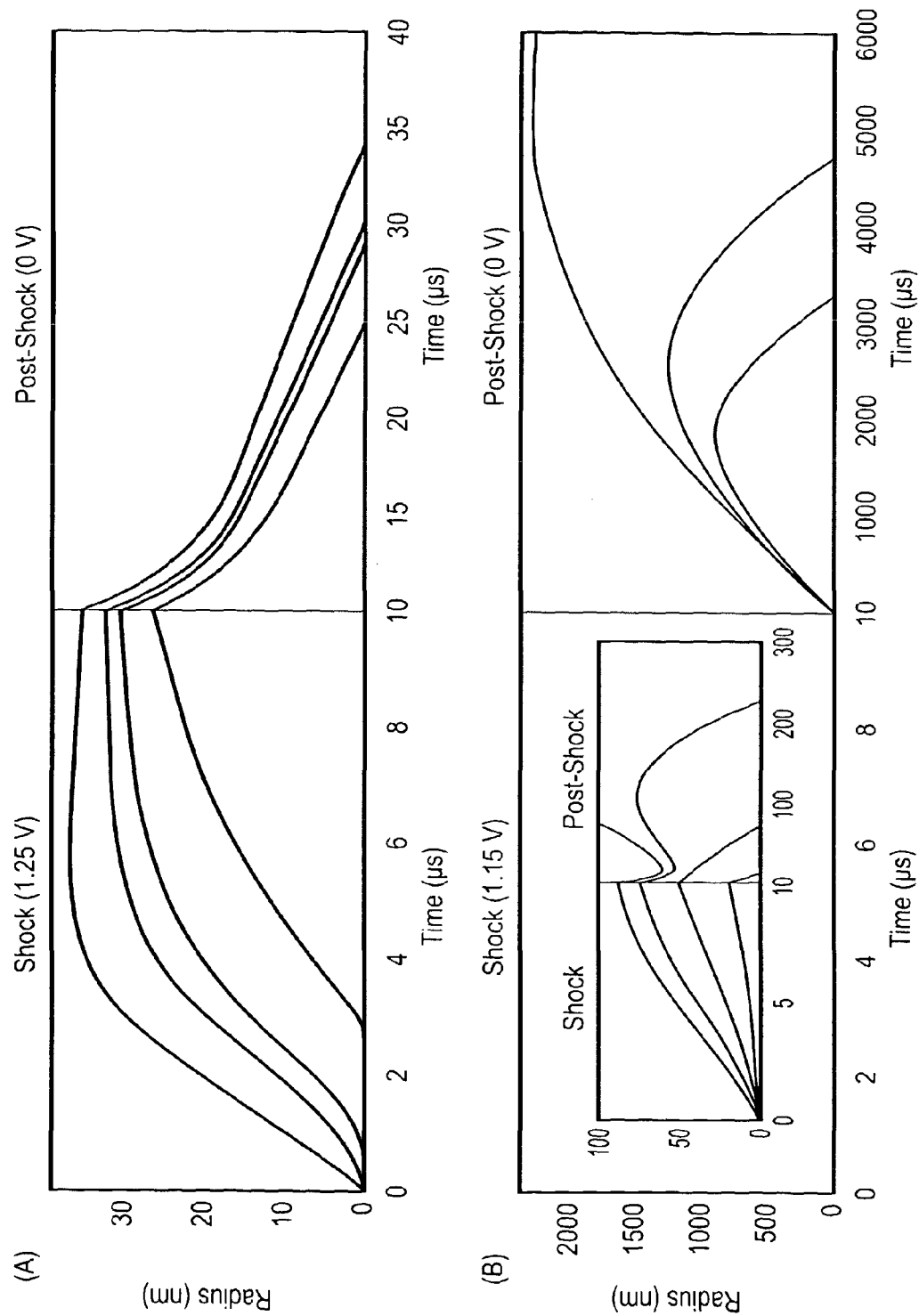
FIG. 4 shows the field flux concentration from a microsphere in a non-homogeneous electric field.

FIG. 4 illustrates one important outcome of pore forming events in a cellular membrane caused by a single electrical pulse. In general high amplitude electrical pulses can cause formation of many small pores that reverses over time and the membrane re-seals. However, a smaller pulse creates a smaller amount of pores of and the newly formed membrane pores can undergo a process called "coarsening" where the resealing eventually does not occur and the pores forms a single very large pore that eventually leads to cell death. This information is important because it illustrates that lower voltage can be used to cause more damage than high voltage, so the optimal effect is not necessarily achieved by the highest amplitude and highest frequency.

Exposing a cell to a lower voltage gives a relative higher number of irreversible pore forming events compared to exposure with a higher field. The higher field generates many pores but with smaller diameter and they are reversible. The figure illustrates pore radii during a 10 μs pulse and the postshock evolution of pores. The gray scale represents the pore radii distribution (i.e., the number of pores with radii between r and r+dr). Solid lines show the 10, 20, . . . , 100th percentiles of the maximum pore radius, illustrating the evolution of the pore radii in time. (A) Evolution of pores after a 1.25 V pulse, which created 18,025 pores. After the pulse, all pores shrink to rm (the minimum-energy radius of (B) Evolution of pores after a 1.15 V pulse, which created a smaller number of pores, 2772. After the pulse, all pores shrink to rm except the largest pore, which grows to a stable radius of 2.23 μm. (Inset) The pulse and the first 300 μs after the pulse shown on an expanded vertical scale. (Redrawn from Biophys J. 2004 May; 86(5): 2813-2826).

Figure 5:
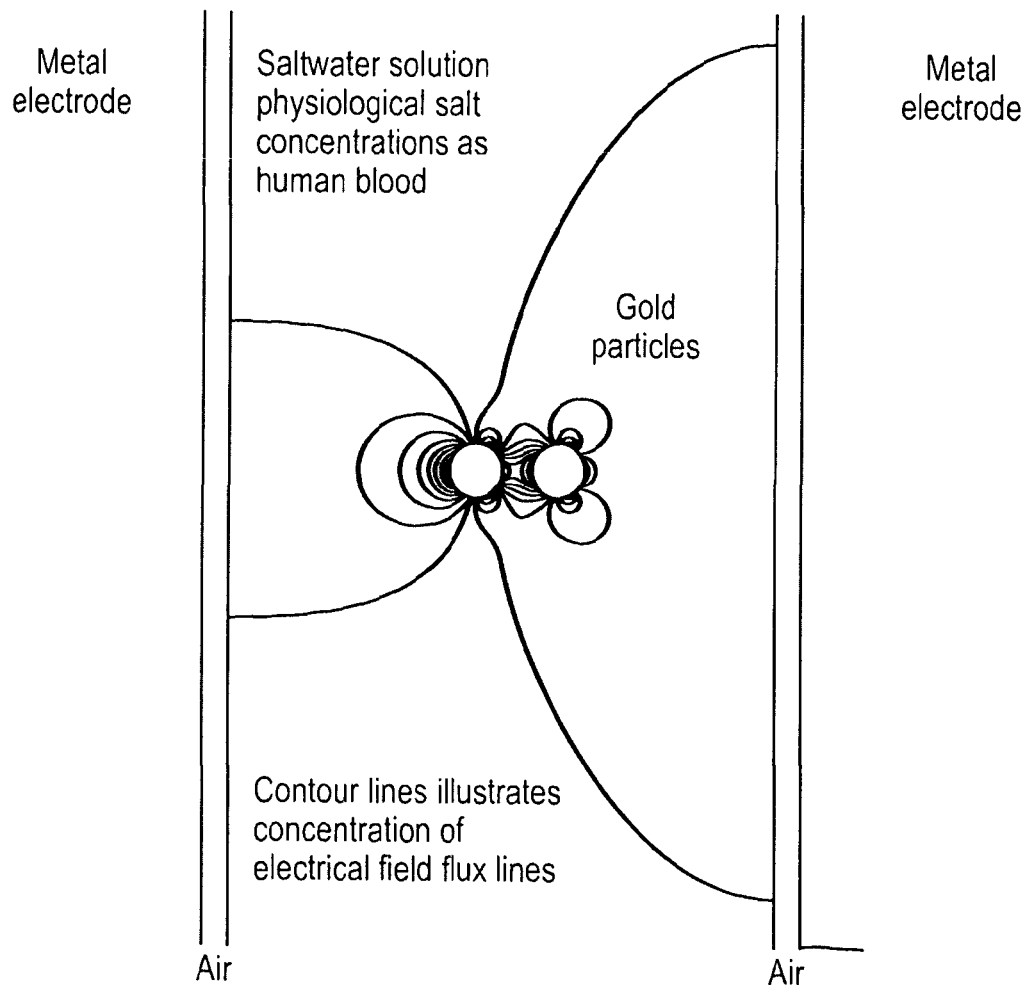
FIG. 5 shows an optimal arrangement of two particles for creating the field flux concentration across the cellular membrane that gives the highest effect.

FIG. 5 illustrates the optimal arrangement between two particles where one is located in the cytoplasma of a mammalian cell and one found on the extracellular side. A similar arrangement is optimal for a spore but where the particles are found on opposing sides of the spore with the same result as the effect described for the mammalian cell.

Plot of results from theoretical model of electrical field flux lines around two gold particles in salt water that has chemical resemblance to human blood. The setup is made by two electrodes with a voltage difference of 300 V separated from the solution with a gap of air. The particles are in the solution. The plot illustrates the field flux concentration effect that can be achieved by positioning two gold particles in proximity of each other. Other metals give similar results. In the model the particles were 1 um diameter gold microspheres. Substantially similar results were achieved for 60 nm and 40 nm diameter gold microspheres.

Figure 6A:
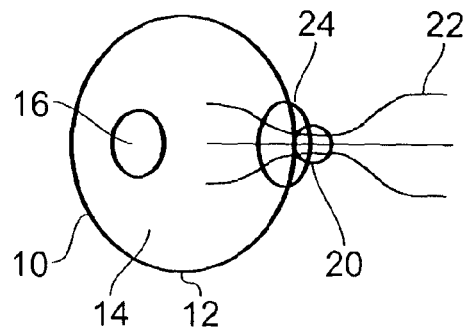
FIG. 6a is a diagrammatical view of a single particle, having a high permittivity, and how this concentrates an electric field adjacent to cell membrane.

FIG. 6a shows an arrangement resulting from an embodiment of the method of the invention in which a cell 10 having a membrane 12, cytosol 14 and nucleus 16 has a particle 20 that is either conductive or has a high permittivity is associated with the extracellular side of the cell membrane. When an electric field, in a direction indicated by the symbol E and shown by means of field lines 22, is applied to the cell and the surrounding medium the field is enhanced by the particle in a region 24 incident on the cell membrane (note the appearance of field lines in the extracellular medium is symbolic and not intended to be accurate representation). With appropriate choice of field strength the enhanced field in the region 24 is sufficient to induce irreversible pore-forming events in the membrane in this region.

Figure 6B:
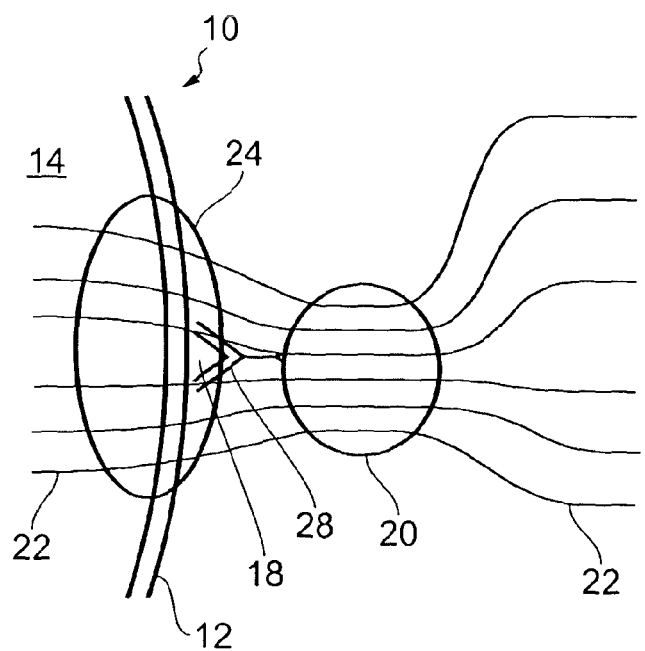
FIG. 6b is a diagrammatical view of a particle bound to target molecule at the target cell surface by a ligand forming part of a coating.

FIG. 6b shows a preferred version of the embodiment in which the particle 20 is bound to a target molecule 18 on the cell surface by means of a ligand 28 provided as part of a coating on the particle. The ligand 28 may be chosen to be specific for target molecules 18 that are present only or preferentially on target cells, so allowing targeted binding of particles 20 to target cells and no, or lesser, binding to non-target cells. The ligand may in some embodiments be adapted to bind to a specific region of a target molecule, for example an extracellular region of a transmembrane protein.

More than one ligand type may be present on a particle, and the ligands may be targeted to the same or different target molecules or molecular regions. The target molecule may be any molecule, such as a protein, protein complex, or sugar. The target molecular region may for example be a region of the protein or one protein in a complex. The embodiment in FIG. 6b therefore provides novel targeted destruction of target cells in a mixed cell population by means of irreversible electroporation of the cell membrane mediated by high permittivity or conductive particles.

Figure 6C:
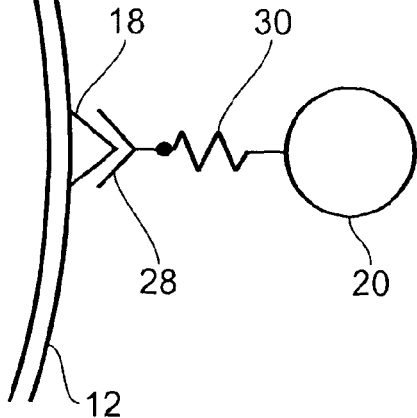
FIG. 6c is a diagrammatical view of a particle spaced from the ligand by a linker.

In a further preferred version of the embodiment shown in FIG. 6c a ligand 28 may be attached to the surface of the particle by a linker molecule 30, which gives the advantage of controlling the mean distance of the particle from the lipid bilayer of the cell membrane, so controlling and optimising the effect of field enhancement on pore formation in the membrane.

Particles in this embodiment are preferably of higher permittivity than the mean permittivity of the environment in the region surrounding them, that region comprising one or more of the extracellular fluid; extracellular matrix; cell membranes of other cells; cell surface molecule such as membrane proteins and sugars. The permittivity of the surrounding medium is therefore a composite permittivity derived from the presence and permittivities of the various components, and therefore may tale a range of values up to that of physiological saline or blood.

Particles may have characteristics as disclosed herein, for example having a dielectric or conductive core, for example a metal core, such as gold, and a coating comprising at least one ligand targeted for a target molecule on the cell membrane. Such ligands may comprise antibodies, aptamers, protein binding partners and peptides, as known in the art.

Figure 6D:
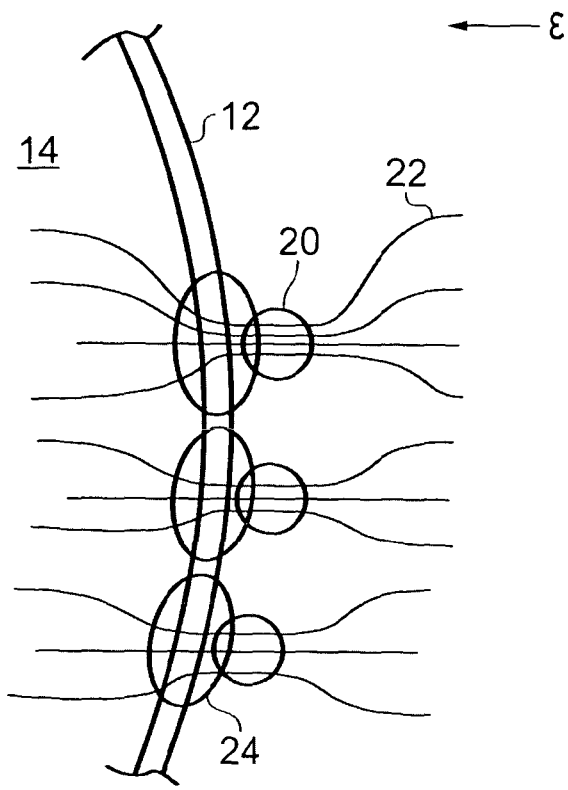
FIG. 6d is a diagrammatical view of multiple particles with high permittivity or comprising a conductive core, adjacent to a cell membrane I.
Figure 6E:
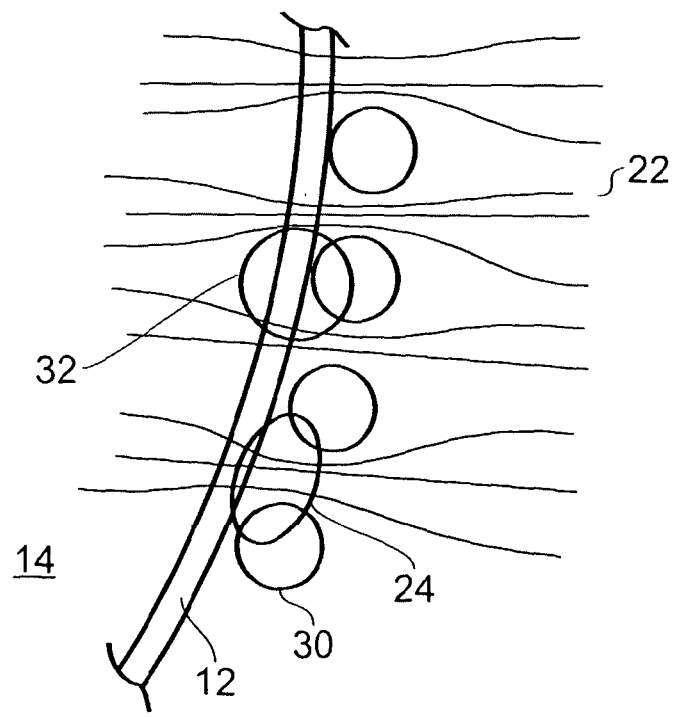
FIG. 6e is a diagrammatical view of multiple particles with low permittivity adjacent to a cell membrane—so concentrating field lines in the medium between them.

FIG. 6d shows an arrangement of particles in an embodiment of the invention, comprising a plurality of high permittivity particles associated with a cell membrane 12. A number of regions 24 of enhanced field strength are formed, which together may serve to destabilise the membrane 12 so as to reduce the threshold applied field for irreversible pore formation. FIG. 6e shows an arrangement of particles in a further embodiment in which a number of particles of permittivity lower than that of the surrounding environment are associated with, for example bound to, the cell membrane.

In this case the field is enhanced in a region 24 located approximately between two particles, but in most embodiments the effect is less than that of field enhancement by one or more high dielectric particles and ideally requires a significant number of particles to be associated with the cell and positioned close to one another in order that the field be enhanced significantly. Effective reduction of the threshold for irreversible electroporation requires more particles in general than in the case of high permittivity particles acting together. While this embodiment is functional, the inventive use of higher permittivity or conducting particles in alternative embodiments is therefore an improvement over the use of insulating or lower permittivity particles, or carbon nanotubes, which have a relatively low permittivity unless oriented precisely with respect to the cell membrane, which in general will not be the case.

FIG. 7a shows an arrangement resulting from use of a further embodiment of the method of the invention, which comprises providing particles adapted to enter a target cell, allowing at least one particle to enter, and then exposing the cell and at least one particle to an electric field, so causing enhancement of the field in the vicinity of the particle resulting in cell death through primarily non-thermal means, in preferred embodiments through irreversible electroporation of the cell membrane. A cell as described before now has a particle 40 provided within it, which may be a dielectric particle, in some embodiments of high permittivity as described above, in alternative embodiments may be conductive, for example comprising a metal, for example gold. As is shown in FIG. 7b a particle within the cell close to the membrane produces a region 24 of enhanced field in the membrane in the vicinity of the particle, so reducing the threshold for irreversible electroporation. The effect is greater for particles close to the membrane than for particles further away in the cytosol. Cells having such a particle within them may therefore be killed while neighbouring cells without particles are undamaged. In preferred embodiments the particles 40 are either adapted to associate with the cell membrane 12 or are present in sufficient quantity within the cytosol that at least one particle will be located close to the membrane without binding to it.

FIG. 7d shows a preferred embodiment in which the internal particle comprises a coating having at least one ligand adapted to bind to a target molecule on the inside of the cell membrane. The particle and ligand may be as described above, the particle being further adapted to enter the cell through the cell membrane. Such entry may be by means of endocytosis as known in the prior art and described in the summary of the invention and below.

Figure 7E:
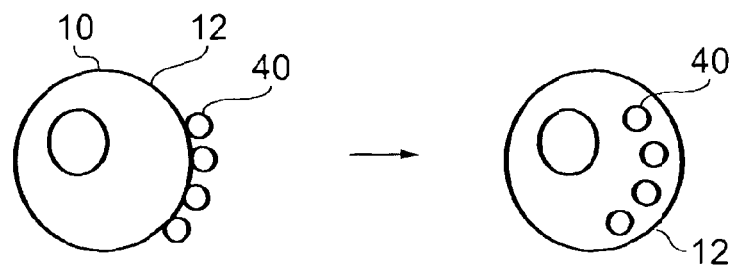
FIG. 7e is a diagrammatical view showing how multiple particles, associated with the exterior of cell membrane, are taken into the cell by endocytosis.

The particles may be targeted to target cells in a similar manner as described above. For example, in FIG. 7d the target molecule at the interior side of the membrane may be specifically or preferentially expressed in a target cell type, so that location of particles at the inside of the cell membrane occurs specifically or preferentially in target cells rather than in non-target cells. In a further embodiment as shown in FIG. 7e the particles 40 may be targeted to associate readily with the exterior of a cell, so providing an increased surface coverage of particles that are then able to undergo endocytosis.

Figure 7F:
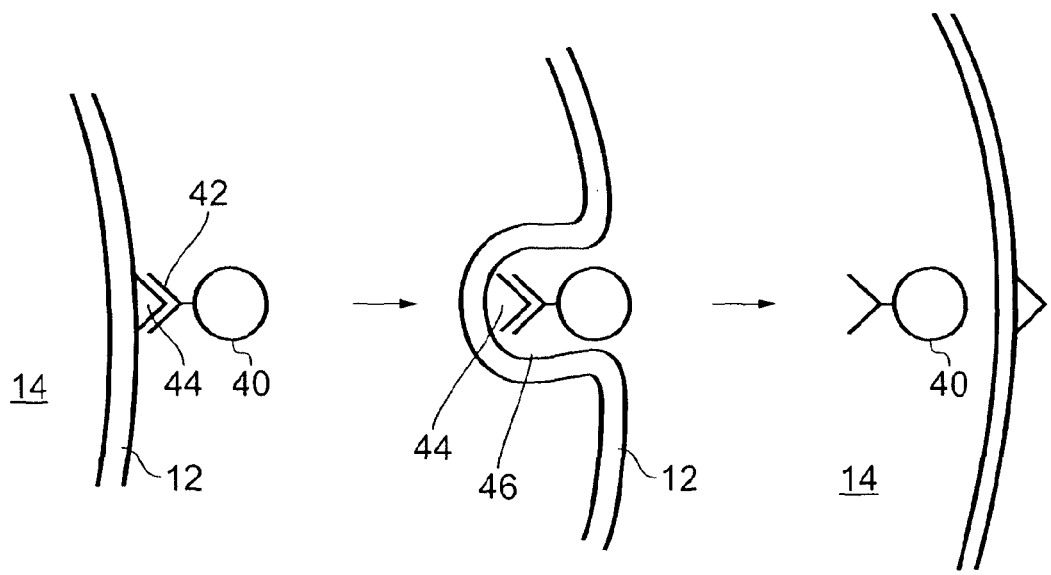
FIG. 7f shows an embodiment where particles are adapted to bind to the exterior of the cell membrane to provide a population of cells in position for endocytosis.

FIG. 7f shows how this might be done preferentially in target over non-target cells. Particles 40 adapted for preferential endocytosis by target cells have a coating comprising at least one ligand 42 adapted to bind to a target molecule 44 which may be preferentially expressed on target cells. This then leads to a population of particles 40 bound to the surface. At least one particle then preferably undergoes endocytosis as shown in FIG. 7f, with the cell membrane forming an invagination 46 that results in the entry of the particle and reformation of the membrane 12. FIG. 7f shows a particle adapted for endocytosis is bound to a target molecule at the exterior of the cell membrane. After a time the particle is taken into the cell by endocytosis and the membrane re-forms. The target molecule is shown left in the membrane but it may be degraded by the cellular machinery once inside the cell.

Figure 7G:
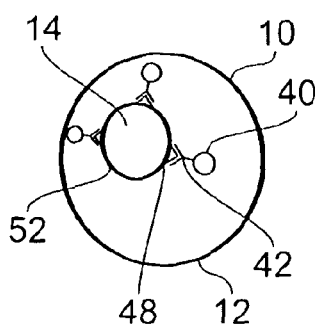
FIG. 7g shows multiple particles inside the cell adapted to bind to a target molecule on the exterior of the nuclear membrane.
Figure 7H:
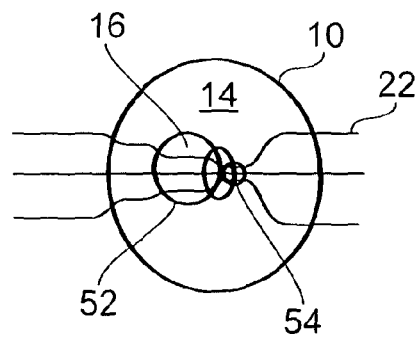
FIG. 7h shows how enhancement of field lines, adjacent the nuclear membrane leads to poration of the nuclear membrane and cell death.

In another embodiment as shown in FIG. 7g the method of the invention is applied to cause cell death by means of destructive effects on the nuclear membrane resulting from enhancement of an applied electric field by particles bound to the nuclear membrane. FIG. 7g shows particles 40 associated with target molecules 48 on the nuclear membrane by means of ligands 42 provides as part of a coating on the particles. FIG. 7h shows a local field enhancement in region 24 of the nuclear membrane caused by particle 40 bound to it.

Figure 8A:
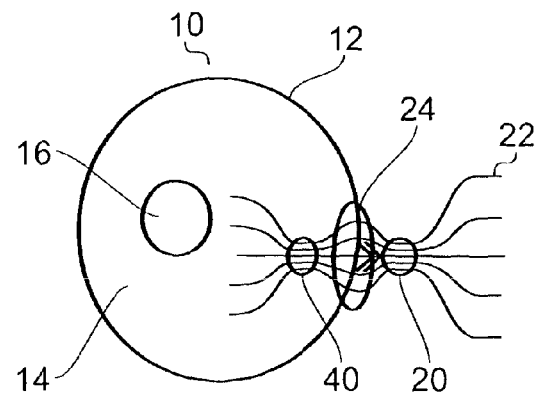
FIG. 8a is a diagrammatical view and shows how a first particle inside and a second particle outside give additional field enhancement.
Figure 8B:
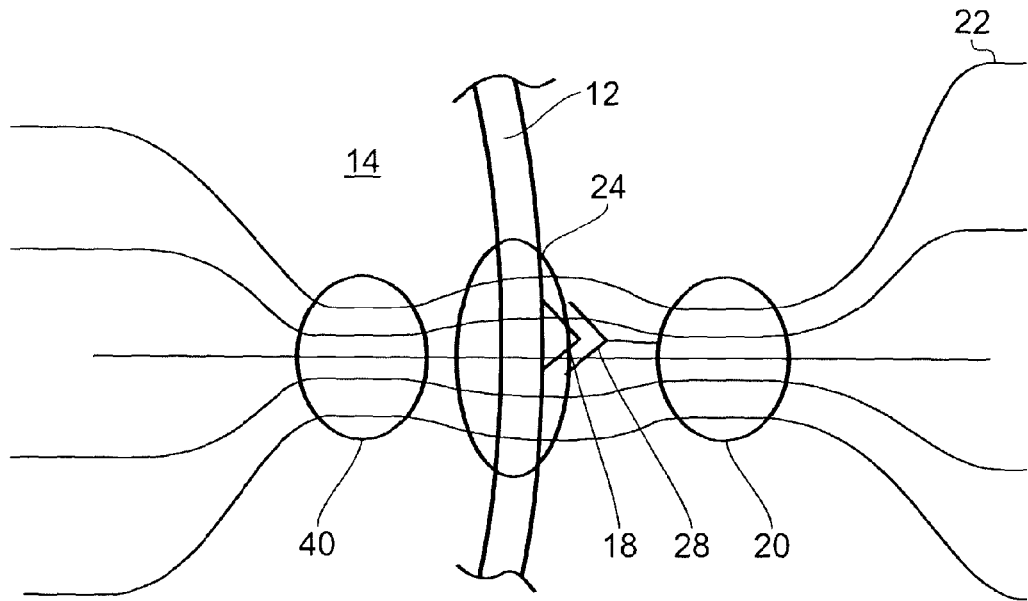
FIG. 8b depicts the situation where a first particle, inside the cell, is not adapted to bind to a target molecule and a second particle, outside the cell, is bound to a target molecule.

FIGS. 8a and 8b show a further arrangement of particles and target cell arising from a further embodiment of the method according to the invention. As shown in FIG. 5, it has been found that two particles may act co-operatively to create a significantly greater enhancement of an applied field than a single particle alone. FIG. 8a shows a cell 10 having a first particle 40 within the cytosol and a second particle 20 bound to the exterior of the cell membrane 12. The two particles may be dielectric particles and may have a high permittivity or have a conductive core, for example comprising a metal such as gold or a metal oxide, such as $Fe_3O_4$. The two particles cause a great enhancement of the electric field in their vicinity, and especially between them, and in any region of the cell membrane adjacent to them, shown here as a region 24 between the particles.

FIG. 8b shows the case in which the first particle 40 is adapted to enter the cell and is present within the cytosol, but is not adapted to bind specifically within the cell, while the second particle 20 is bound to a target molecule 18 by means of a ligand 28 as described before. Enhancement of the field is shown in FIGS. 8a, 8b by means of the increased concentration of field lines in the vicinity of the particles compared with in the environment surrounding them.

In preferred embodiments of the invention, first particles 40 are adapted to enter the cell, and second particles 20 are adapted to bind to the exterior of the cell. One or both of the first and the second particles may be targeted to target cells. The first particles 40 may be adapted to enter target cells preferentially as described above, and may be adapted to bind to a specific location or range of locations with the target cell. Alternatively, the first particles may be simply adapted to enter both target and non-target cells. The second particles are preferably adapted to bind to target molecules on the exterior of the target cells as described above.

The situation resulting from the method of the invention in this embodiment is that target cells have a particle arrangement associated with them, comprising at least one first particle within the cell and at least one second particle bound to the exterior of the cell membrane, as shown in FIGS. 8a and 8b. The adaptations of one or both of the particles to associate with or to enter target cells selectively are such that non-target cells do not have this particle arrangement.

Figure 8C:
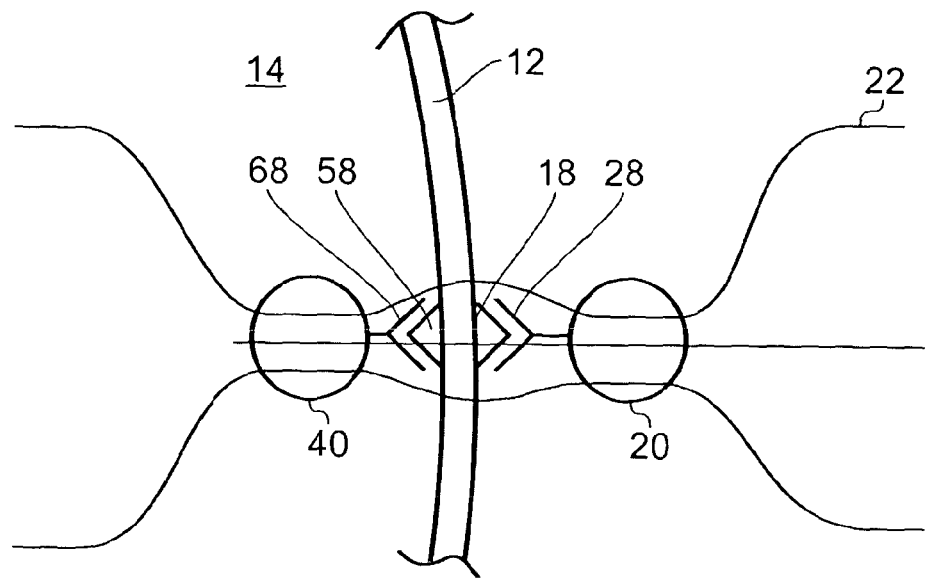
FIG. 8c shows a first particle, inside the cell is adapted to bind to a target molecule or target molecular region on the inside of the cell membrane.

FIG. 8c shows an arrangement of particles arising from a further embodiment of the invention, in which the first particle 40 in the interior of the target cell is bound to a target molecule at a target molecular region 58 located at the interior of the cell membrane, by means of a ligand 68 provided as part of a coating on the particle, while a second particle 20 is bound to a target molecular region 18 at the extracellular side of the membrane. In this case the target molecular region on the inside is shown as an intracellular portion of a transmembrane protein, with the second particle adapted to bind to extracellular portion of that protein.

In a preferred embodiment the regions 18 and 58 are regions of the same target molecule, such as a transmembrane protein, for example a receptor or ion channel. This arrangement is advantageous as the first and the second particle are both bound in proximity to the cell membrane and to each other and highly effective field enhancement results.

Figure 8D:
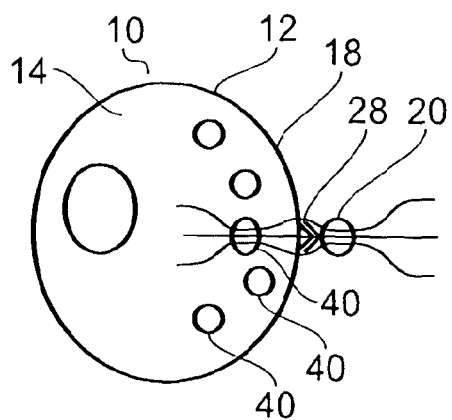
FIG. 8d shows a number of first particles are in various positions within the cell. The field is enhanced primarily by the first particle that is closest to the second particle outside the cell.

FIG. 8d shows an arrangement of particles arising from a further embodiment of the invention, in which a number of first particles 40 are located within the cytosol, either at random or bound to locations with the cytosol, and a second particle 20 is bound to a target molecule 18 on the cell membrane. Effective field enhancement occurs between the second particle and the first particle that is nearest to it, showing that precise location of the first particles is not necessary provided sufficient first particles are present within the cell that when a second particle binds it will be in proximity to at least one first particle.

Figure 8E:
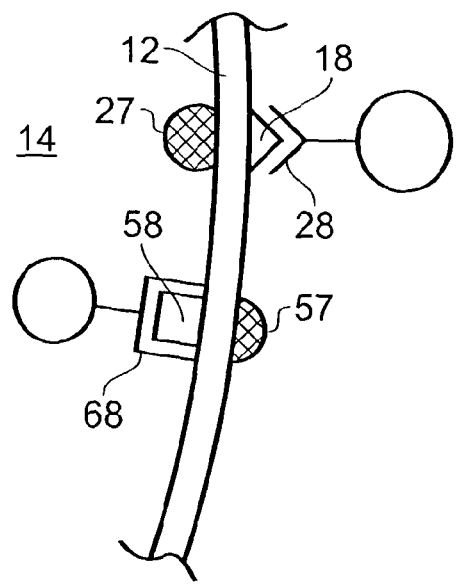
FIG. 8e depicts how a first particle, inside the cell, is adapted to bind to a first target molecule on the cell membrane; and how a second particle, outside the cell, is adapted to bind to a second target molecule.
Figure 8F:
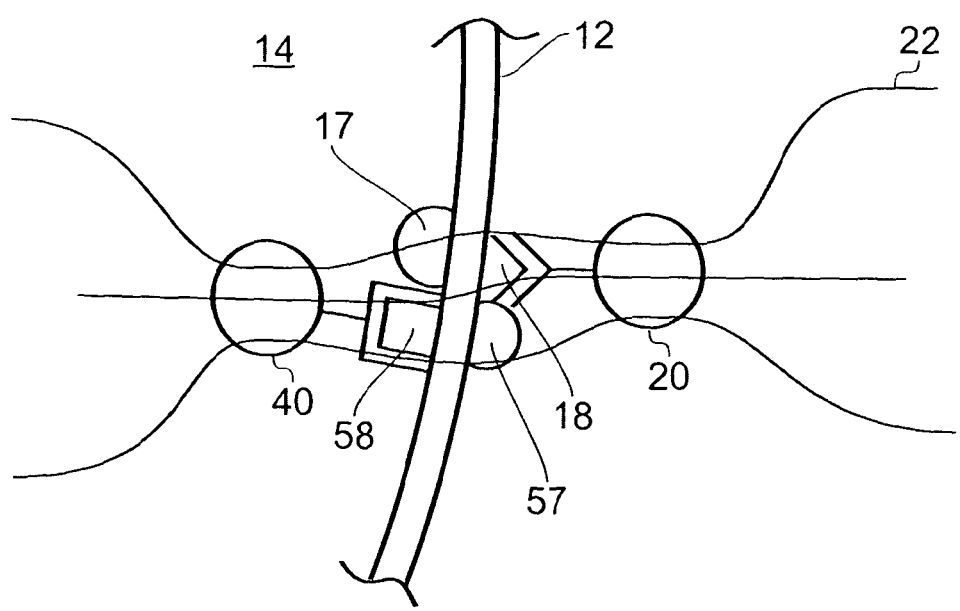
FIG. 8f is a similar view to FIG. 8e, but depicts first and second target molecules closer together so field enhancement is greater than that shown in FIG. 8e.

FIG. 8e shows an arrangement of particles arising from a further embodiment of the invention, in which the first and second particles are bound to target molecular regions 58, 18 on different target molecules, shown as having non-binding regions 57, 17 respectively. As shown in FIG. 8f, field enhancement is most effective when the target molecules are close together in the membrane. It is within the scope of the invention to select the ligands 68, 28 provided as part of a coating on the first and second particles to achieve this situation. Certain target molecules are known to be mobile within the membrane, and it is within the scope of the invention that the application of a field may induce forces on the first and/or second particle that may cause movement of the particle relative to the target cell or cell membrane, movement or distortion of the cell membrane, or movement of cell components or target molecules to which the particles are bound. Such movement may lead to increased effectiveness of causing cell death according to the invention, for example by the first and second particles moving to become closer together in response to the applied field, so acting to increase the field enhancement in their vicinity.

FIG. 8f depicts how field enhancement is optimised if target molecules are chosen so that they are close together in the cell, or are expressed in large numbers, thereby improving the chance that the first and the second particles bind close together. The first and the second target molecules may be mobile within the cell membrane and may associate together.

Figure 9A:
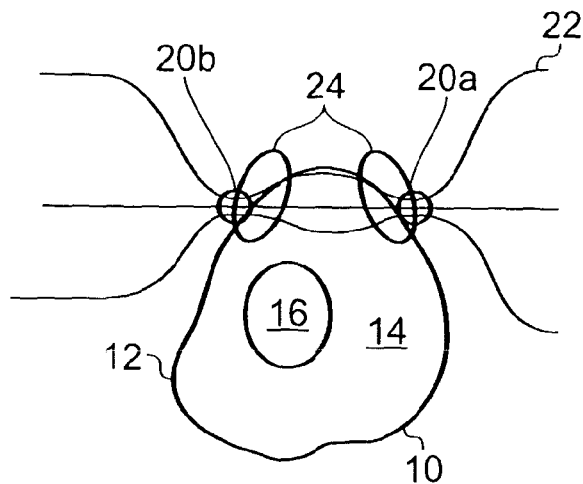
FIG. 9a shows two particles having a high permittivity or conductive, (such as metal particles), bind to the exterior of a cell and produce an enhanced field in the vicinity of the cell membrane.

FIG. 9a shows an arrangement of particles arising from a further embodiment of the invention, in which at least two particles 20a, 20b are bound to the exterior of a target cell. Enhancement of the applied field occurs when the particles are located in proximity to one another. Regions of enhanced field intersect the cell membrane according to the position of the two particles, the shape of the cell, and the orientation of the particles with respect to the applied field. While only two particles are shown it will be appreciated that in this embodiment, the method advantageously provides sufficient particles to the target cell that there will be on average at least one such arrangement of particles associated with the cell.

Figure 9B:
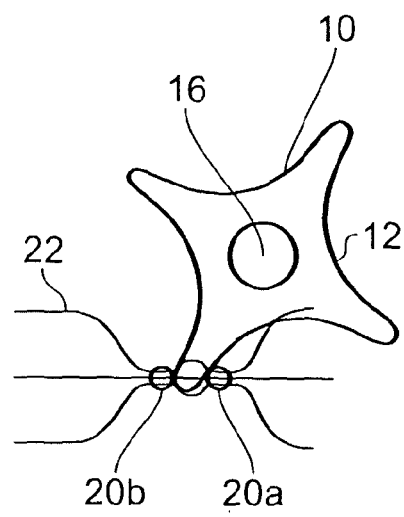
FIG. 9b shows how, in some cell morphologies, two particles on the exterior of the cell are located close together on opposite sides of a region of the cell in the direction of a component of the field.
Figure 9C:
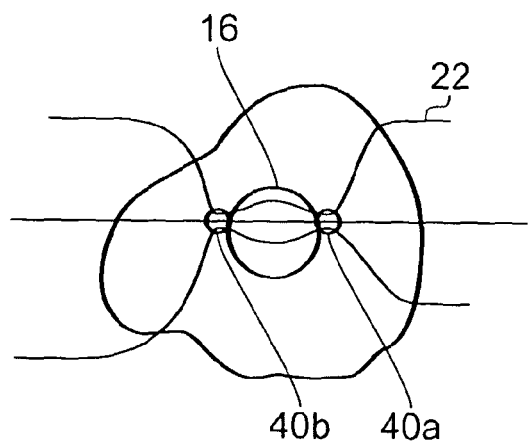
FIG. 9c shows how two particles bound to the exterior of the nuclear membrane, that are closely located, produce field enhancement in a region of the nucleus sufficient to lead to cell death, for example by electroporating the nuclear membrane.

FIG. 9b shows a particle arrangement that may arise at a region of a target cell with higher aspect ratio, for example a process or outgrowth, for example as in neuronal cells. FIG. 9c shows an arrangement of particles arising from a further embodiment of the invention, in which the particles are adapted to enter the cell and to associate with the nuclear membrane, so causing field enhancement across a region of the nucleus and nuclear membrane, resulting in cell death through non-thermal means, in some embodiments through disruption of the nuclear membrane.

Figure 10A:
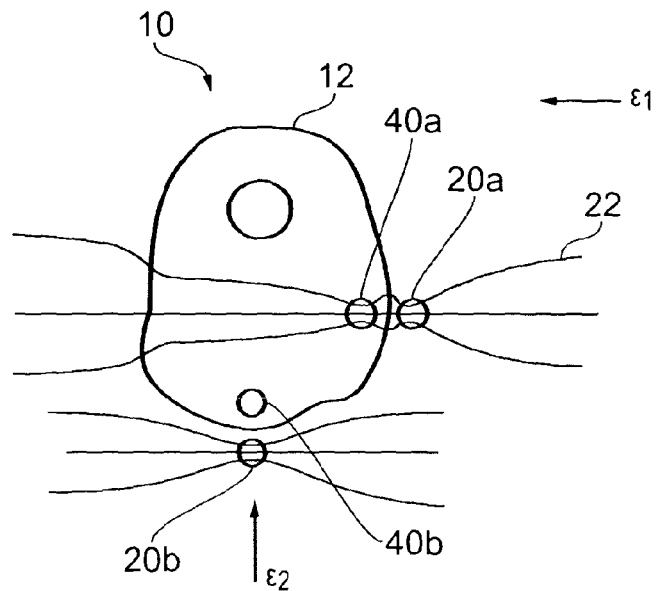
FIG. 10a shows diagrammatically the significance of field orientation relative to orientation of pairs of particles and how a first field direction E1, for a first pair of particles, produces a greater effect of field enhancement on the cell membrane than a second pair of particles, for a second field orientation E2, produces a greater effect.

In a further embodiment of the invention, the orientation of the electric field may be controlled or varied with respect to the target cells, a group of target cells such as a tumour, or the body of a subject hosting the target cells. FIG. 10a shows an arrangement of particles arising from an embodiment of the invention, and illustrates that the orientation of the field with respect to one or more target cells may in some embodiments affect the degree of field enhancement. In FIG. 10a a first particle arrangement 20a, 40a has the axis of the particle arrangement—the line joining the two centres of the particles—aligned with the field direction E1. This is expected to lead to a higher degree of field enhancement in the region of the membrane near or between the particles. A second particle arrangement 20b, 40b has its axis perpendicular to the E1, which is expected to lead to lesser field enhancement in the region of the membrane near or between the particles. Field in direction E2 reverses this situation. It is clear that for a random orientation of particles arrangements around a target cell, the best chance of achieving high field enhancement is through using multiple orientations of the applied field.

Figure 10B:
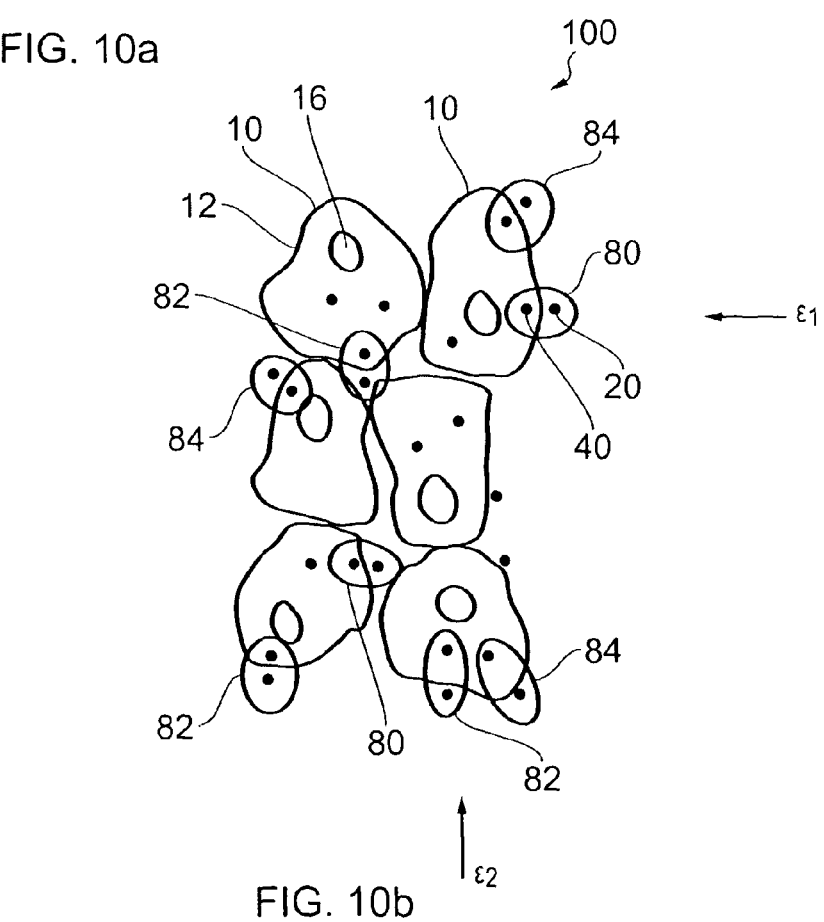
FIG. 10b is a diagrammatical representation of random provision of particles to a number of target cells in a region of tissue and shows for a first field direction E1 certain particle pairs or arrangements produce a greater effect than others.

FIG. 10b shows an arrangement of particles arising from a further embodiment of the invention, the particles being provided within a region of tissue 100 comprising a number of target cells 10. Particles targeted to these cells will in general be distributed randomly and so within the tissue particle arrangements 80, 82, 84 resulting from the invention will be oriented randomly. For a first field direction E1 certain particle pairs or arrangements (80) will produce a greater effect than others (82). For a second field direction E2 the reverse is true. Some particle arrangements (84) will have an intermediate level of effect for both field directions. Therefore varying the orientation of the applied field with respect to a group of target cells, or the tissue or body of a subject in the case of treatment of disease, is advantageous and may be achieved by the method and apparatus of the invention.

Figure 11A:
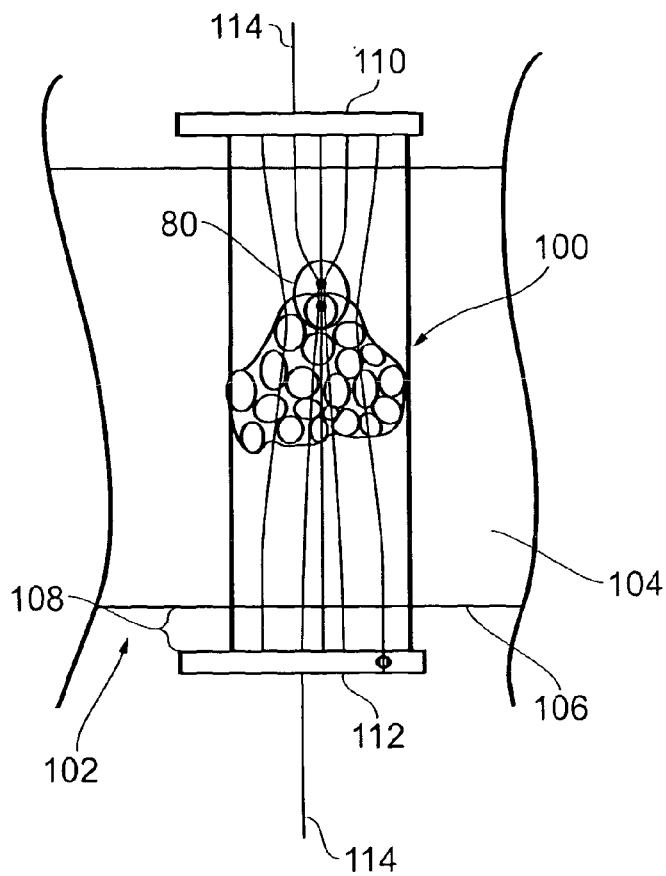
FIG. 11a shows in diagrammatical form treatment of target cells, within a region of tissue within the body, for example a tumour, using planar electrodes external to the body.

In accordance with the invention, the electric field may be applied by electrodes disposed in a variety of ways around the body. In contrast with prior art methods, the field enhancement of the invention allows a greater variety of electrode placement to be used. Electrodes may be located external to a region comprising the target cells, such as a container, tissue, or body of a subject. It is a particular advantage of the invention that the applied field can be lower than in the prior art, and some embodiments use electrodes placed externally to the body of a subject. For example, FIG. 11a shows treatment of target cells within a region of tissue 100, for example a tumour within the body 102 of a subject, the field being applied by a first electrode 110 and a second electrode 112, connected to a source of potential, such as a device according to the invention by means of connections 114. In this embodiment the electrodes are planar electrodes external to the body. The electrodes are shown separated from the body by a gap 108. In an alternative embodiment one or both electrodes may be in contact with the skin 106. The electrodes may be flexible or adapted to conform to the contours of the body, or may be shaped to maintain a given separation from the body.

Figure 11B:
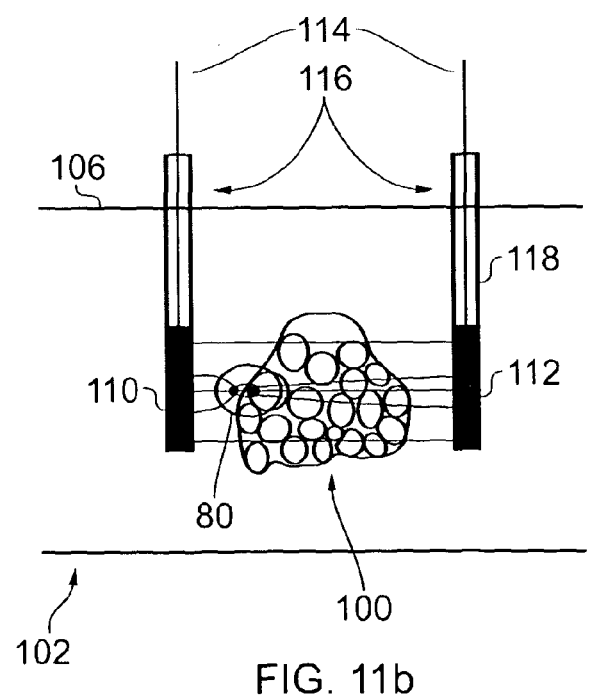
FIG. 11b shows in diagrammatical form treatment of target cells, with the use of electrodes, implanted in the body, and illustrates the effect of different field orientations on different orientation of particle arrangements.

FIG. 11b shows treatment of target cells within a region of tissue 100 using implanted electrodes 110 and 112, each forming part of implanted probes 116. The probe 116 has one or more conductive regions adapted to provide a region of electric field within the body and one or more insulated regions 118. Probes suitable for use in this mode are known in the prior art.

Figure 11C:
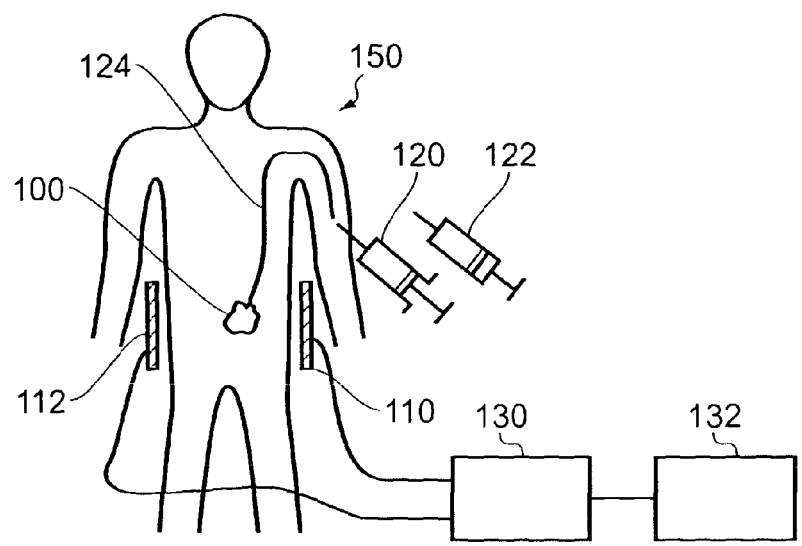
FIG. 11c shows in diagrammatical form treatment of target cells at a region within the body.

FIG. 11c shows a method and an apparatus for treatment of a disease within a subject by means of destruction of target cells at a region within the body. Particles are administered systemically to a subject 150 for example by means of injection or infusion into the blood stream. According to the method of the invention, a composition 120 comprising a first particle type is administered, the particles travel to the region 100 through the circulatory system 124, and associate with the target cells. After a chosen time interval t1, chosen to allow particles to reach their desired locations and arrangement(s) with respect to the target cells, a field is applied by electrodes 110 and 112, potentials on the electrodes being provided and controlled by a device 130, optionally under the control of a programmable unit 132. The electrodes are shown as being external electrodes distanced from the body, though any form or location of electrodes as disclosed herein may be used. The field may be re-applied at intervals.

In a further embodiment, the first composition 120 is administered as above, a chosen time interval t1 is allowed to elapse, and then a second composition 122 comprising a second particle type is administered. A second time interval t2 is then allowed to elapse, and the field is applied as described above.

In preferred embodiments the first particle type is adapted to enter cells (either all cells, or target cells selectively) as described above and the second particle type (where used) is adapted to bind selectively to the exterior of target cells but not to non-target cells. In an alternative embodiment the first and second composition both comprise the same particle type, adapted either to enter the target cell selectively or to bind selectively to the exterior of the target cell. In some embodiments the particles are adapted to remain in position within or associated with the target cells for a period of time within which multiple applications of the electric field may be made.

Figure 11D:
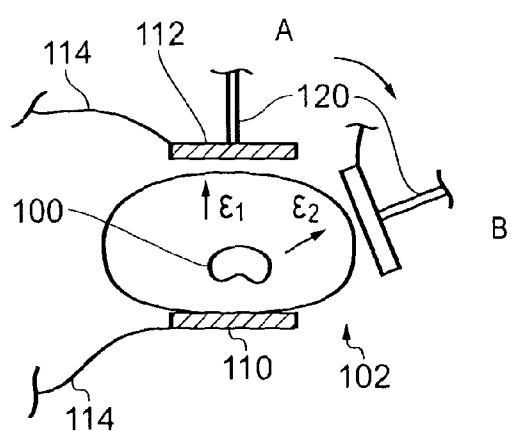
FIG. 11d is a diagrammatical cross section, through a body during treatment, of target cells in a region of the body.

FIG. 11*d* shows a cross section through a body 102 during treatment of target cells in a region 100 of the body. Electrodes 110 and 112 in position A apply a field in direction E1. One or both electrodes may be in contact with the body as shown for electrode 110, or separated from it as shown for 112. Electrode 112 is shown also in an alternative position B that provides a field in a second direction E2. One or both electrodes may be made movable, for example by a clinician or automatically, moved by a motor means (not shown) under the control of the device 130 or programmable unit 132.

Figure 11E:
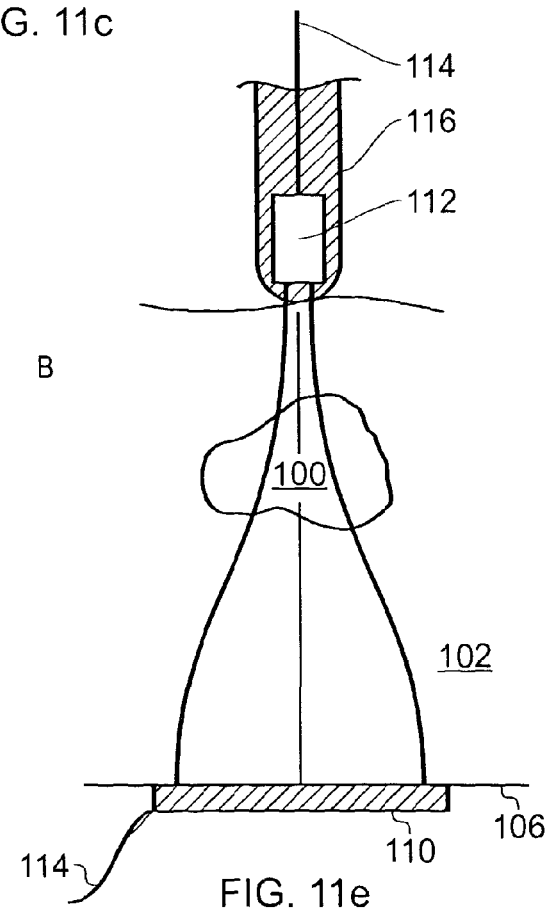
FIG. 11e is a diagrammatical cross section through a body during treatment of target cells in a region of the body, showing a movable electrode, for example a hand-held probe, which may be separated from the skin by an insulating layer 116.

FIG. 11*e* shows a cross section through a body 102 during treatment of target cells in a region 100 of the body. Electrodes 110 and 112 apply a field. Electrode 112 is movable in x and y directions parallel to the skin surface, and may be for example a hand-held probe, and may be separated from the skin by an air gap or in contact with it, separated by an insulating layer 116.

Figure 12A:
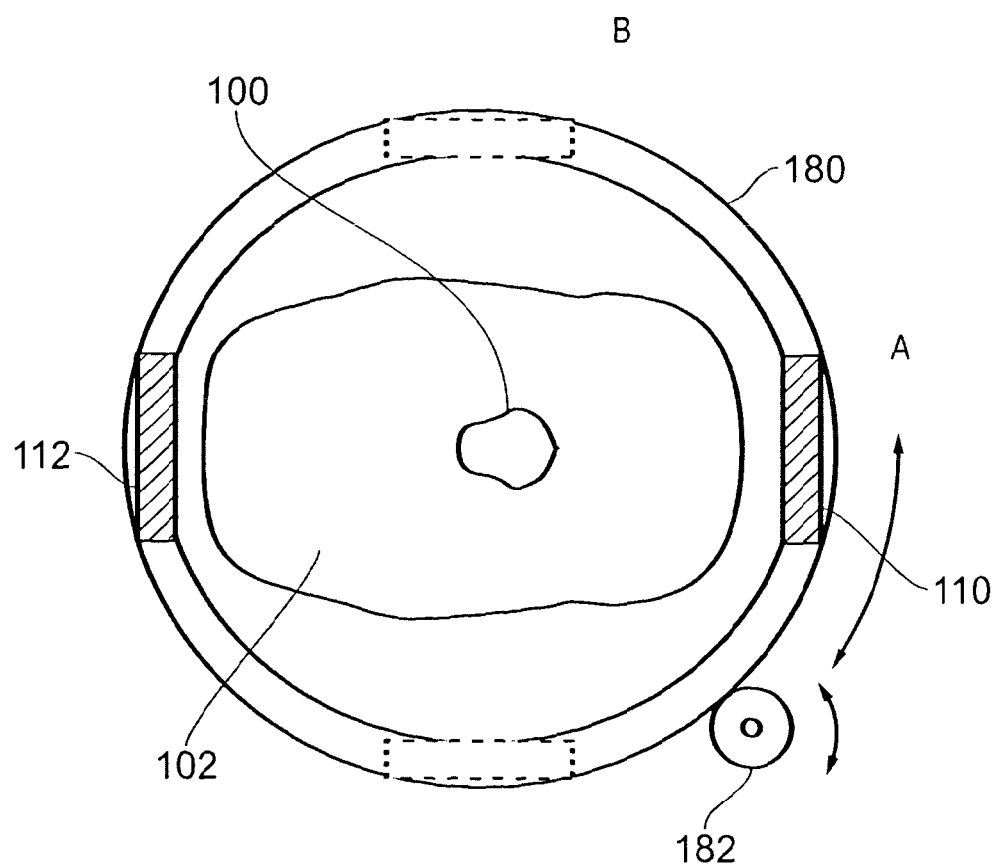
FIG. 12a is a diagrammatical overview, (showing a horizontal cross section through the body of a patient), of an apparatus for moving electrodes around the patient's body during treatment.

FIG. 12*a* shows an embodiment of an apparatus usable with the method of the invention and as part of the apparatus of the invention, for the treatment of disease in a subject, for example by destruction of target cells within a region 100 of a body 102. Electrodes 110 and 112 are mounted in a structure 180 that supports them separated from and close to the body, and is adapted to cause them to rotate around the body as shown by the arrows, so moving them through a range of orientations with respect to the body. This allows the applied field between them to be moved through a range of orientations with respect to the region 100 and the target cells and particle arrangements, within it. For example, the structure 180 might be moved by a motor means 182 coupled to it between a first position A and a second position B, so moving the direction of the applied field through an angle, say 90 degrees. The angle of rotation might be smaller or greater than 90 degrees, and may be chosen according to the location and nature of the region 100, for example it may be up to 180 degrees in one sense or both senses. More than one pair of electrodes may be provided within the structure 180, the pair that is providing the field being selected by a switch means, in order further to control the field direction at any time or point in the treatment process. The structure 180 might rotate about the body 102 in a horizontal plane, e.g. while the subject is standing, or in a vertical plane, e.g. when the subject is lying flat.

Figure 12B:
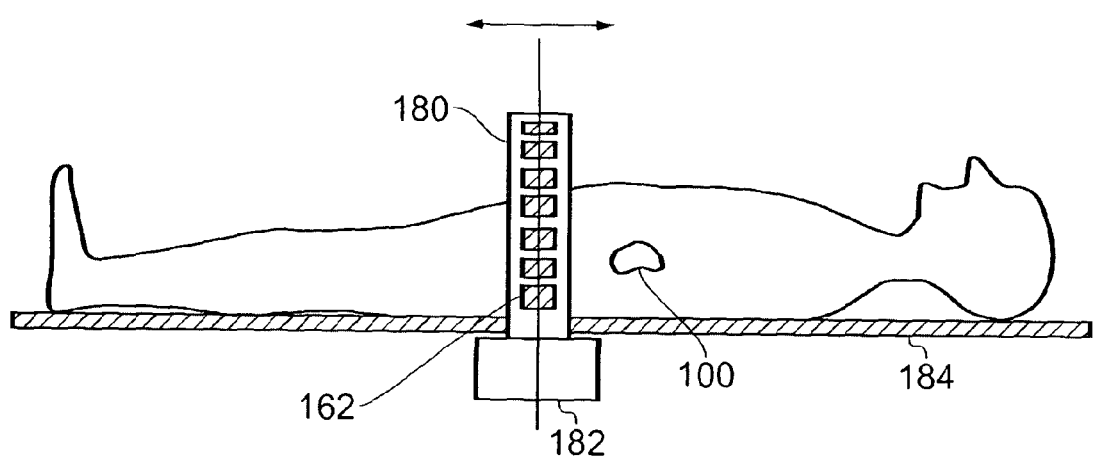
FIG. 12b is a side elevation of the apparatus in FIG. 12a and shows a means for displacing electrodes along the length of a patient's body as well as around the body so as to perform treatment in accordance with the method.

FIG. 12*b* shows a further embodiment of an apparatus usable with the method of the invention and as part of the apparatus of the invention, for the treatment of disease in a subject. Here two or more electrodes 162 (a plurality are shown) are provided within a structure 180 that is now adapted to move in a direction along the body of a subject, shown here as lying flat on a treatment surface or table 184, driven for example by motor means 182. At least one pair of electrodes within the structure 180 are have potentials applied to them so as to generate a field between them as described further for FIG. 12*c*. The structure 180 may then move along the body of the subject in order to subject a range of target cells within the body to the field. It will be apparent that the structure 180 may also rotate around the body as shown in FIG. 12*a* to produce a combined motion and a combined range of electric field directions. Motion in one or both dimensions may be controlled by a control means provided as part of the device of the invention or the programmable unit. In this way target cells may be exposed to a field in both of two dimensions. A further structure 180 (not shown) may be provided separated laterally from and parallel to the first in order to provide control a component of field orientated in the third dimension. Such an apparatus is applicable in cases where target cells are not all localised within a region 100, allowing treatment of large parts of the body without the use of large electrodes.

Figure 12C:
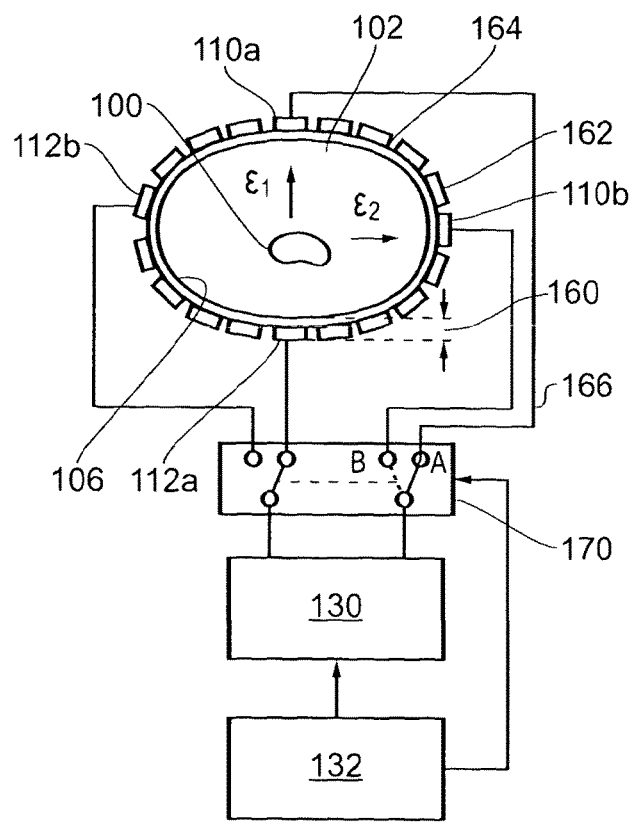
FIG. 12c is a diagrammatical overview of an apparatus and shows multiple electrodes around a region of the body, adaptable to the contours of the body, for example by way of a flexible support structure that is adapted to deform to conform to a patient's body.

FIG. 12*c* shows a further embodiment of an apparatus usable with the method of the invention and as part of the apparatus of the invention, for the treatment of disease in a subject, for example by destruction of target cells within a region 100 of a body 102. Here two or more electrodes are provided as part of an electrode structure 160, which is preferably flexible and may be shaped to, placed around or attached to the body or a body part, for example in the manner of a belt or armband, the electrodes themselves preferably being separated by a thin layer of insulator from the skin 106, but in some embodiments at least one electrode being in contact with it. The electrodes are mounted on a flexible substrate 164 and are connected by leads 166 by means of switch unit 170 to the device 130 and programmable unit 132. The switch unit in use serves to connect pairs of electrode 110, 112 to the device so as to provide the field. As different pairs around the structure 160 are connected, so the field orientation is changed. The switch unit may be controlled by the device or the programmable unit to provide a desired pattern of field orientations during a treatment, shown as for example E1 when electrodes 110*a* and 112*a* are connected by the switch in position A, and E2 when electrodes 110*b* and 112*b* are connected by the switch in position B.

Figure 12D:
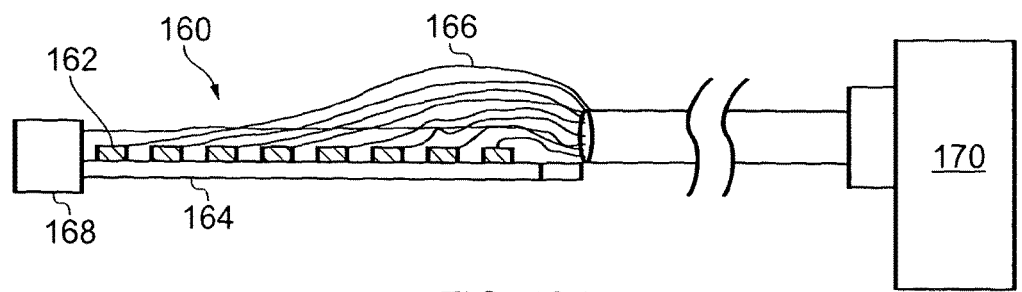
FIG. 12d is a diagrammatical overview of a portion of the apparatus in FIG. 12c, that supports the multiple electrodes, removed from the body.

FIG. 12*d* shows the electrode structure 160 laying flat, optionally provided with a fastening mechanism 168 to fasten the structure to or around the body for example in a semi-rigid configuration or in the manner of a flexible belt.

Figure 13A:
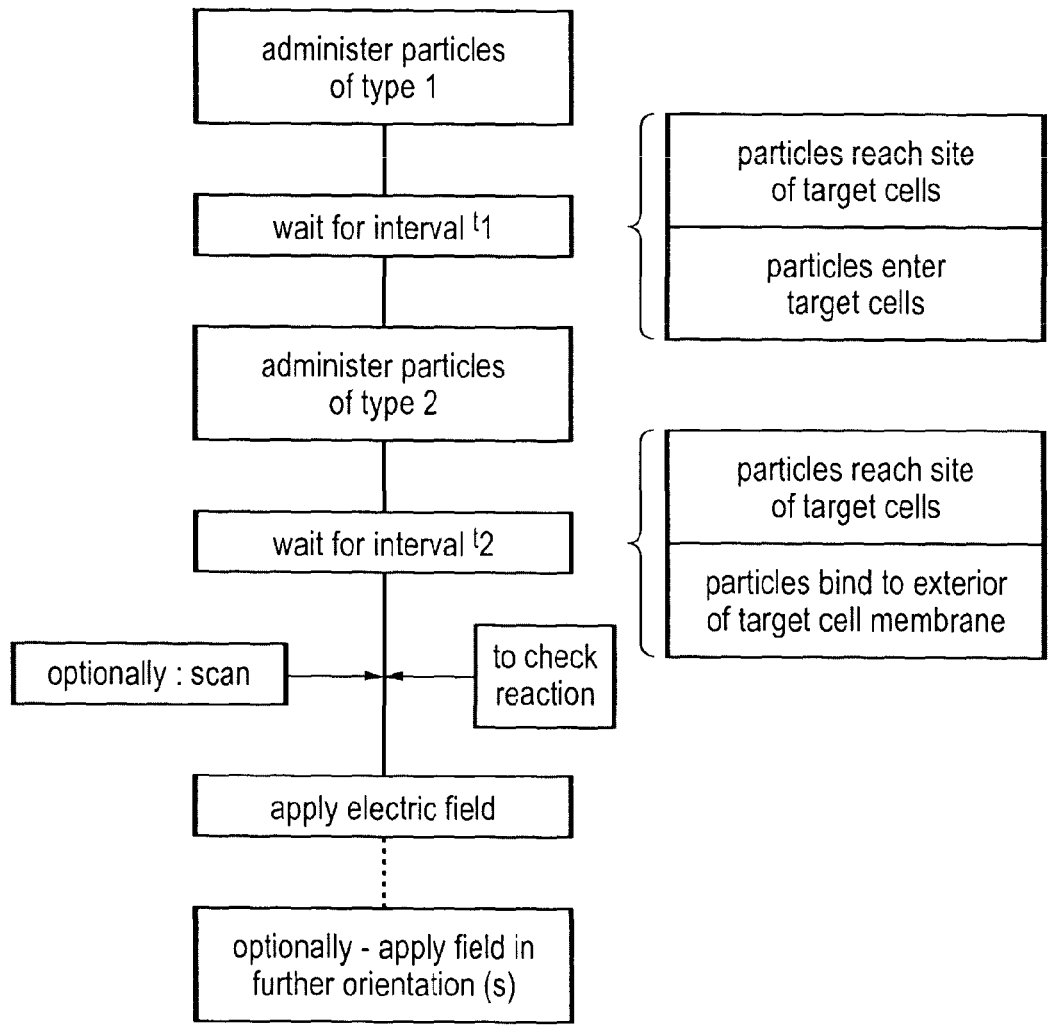
FIG. 13a is a flow diagram showing steps in the method, with a first particle type adapted to enter the target cells and a second particle type adapted to bind to the surface of the target cells.

FIG. 13*a* shows a flow diagram for a method according to the invention, for the embodiment where a first particle type is adapted to enter the target cells and a second particle type is adapted to bind to the surface of the target cells. It is envisaged that multiple applications of the electric field may be made following provision of the particles.

Figure 13B:
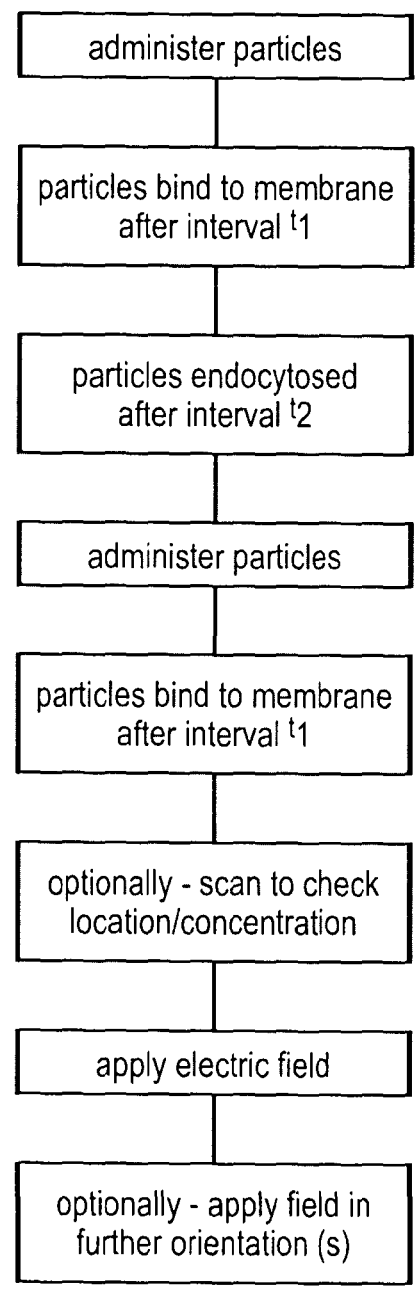
FIG. 13b is a flow diagram depicting an example of the method where a single particle type is used, the particle being adapted to enter the target cell and reside at the surface of the cell before endocytosis.

FIG. 13b shows a flow diagram for a method according to the invention for the case where only a single particle type is used, the particle being adapted to enter the target cell selectively, for example by targeted association with the surface of the target cell before endocytosis as described previously. In this embodiment the location and distribution of the particles is controlled by the timing of administration according to the method. Particles from the first administration are allowed time interval t1 to bind the target cell surface and then be taken into the target cell. After interval t1 the second administration is then made and interval t2 allowed to elapse, to allow the second group of particles to bind to the exterior of the target cells, but t2 is not long enough to allow the particles substantially to be taken into the cells. The field is then applied. In general in this method t2 is less than t1.

Optionally the methods as shown in FIGS. 13a and 13b may include steps of imaging the region 100 to determine the location and number of particles, and hence the readiness for application of the field. Imaging may also be used to determine the effectiveness of the treatment.

Figure 14:
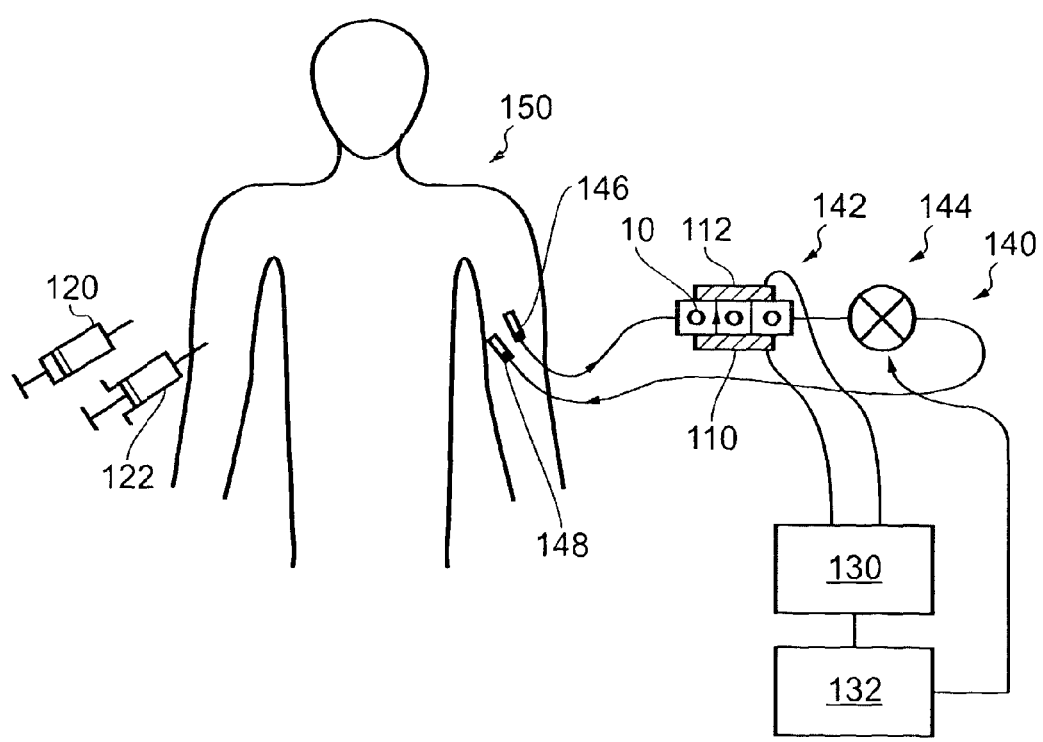
FIG. 14 shows a diagrammatical view of a system for treating target cells in blood; particles are administered into the body and allowed to associate with the target cells and blood is passed through a flow cell where they are exposed to an electric field before returning blood to the body.

FIG. 14 shows a method and an apparatus for treatment of a disease within a subject by means of destruction of target cells suspended in the subject's blood. A composition 120 comprising a first particle type is administered systemically to a subject 150 for example by means of injection or infusion into the blood stream, and particles then associate with target cells within the blood. After a chosen time interval t1, chosen to allow particles to reach the target cells and form desired particle arrangement(s) with respect to the target cells, blood is drawn from the circulation by means of a first cannula 146 and flowed through an extracorporeal flow circuit 140 comprising a flow cell 142 and preferably controlled by a pump or flow control means 144. A field is provided in the flow cell by electrodes 110 and 112 disposed on either side of the flow cell, such that target cells comprising particles are destroyed by the method of the invention on passing through the flow cell, non-target cells being substantially unharmed. Blood is then flowed back to the subject through a second cannula 148.

In a preferred embodiment a second composition 122 comprising a second particle type is administered after the interval t1, and a further interval t2 allowed to elapse before the blood is exposed to the field, the first and second particle types being adapted as described previously.

The method may be carried out by an apparatus comprising element as shown in FIG. 14, namely standard cannulae and extra-corporeal blood flow components and pump or flow control means. Flow cells for conventional electroporation are known. The flow cell forming part of the invention may take any form adapted to allow a sufficient flow rate of blood while applying an electric field to the flow, and may be substantially planar or tubular, for example formed from concentric cylinders. A suitable flow cell comprises two parallel surfaces separated by a flow space, a substantially planar electrode mounted on or disposed above each surface. Electrodes are preferably insulated from the blood in the flow space. The dimensions of the flow cell, the flow rate through the cell, the field intensity profile are all chosen to give effective killing of the target cells while minimising damage to non-target cells. Flow may be continuous or may be intermittent. Flow and field pulse profile may be controlled by the device 130 or programmable unit 132.

In a further embodiment the method further comprises the step of fractioning the blood and applying the method of the invention to a blood fraction that contains the target cells. In this embodiment blood is withdrawn from the subject and processed by conventional apheresis techniques, the desired fraction being withdrawn from the apheresis process to be treated using the method and apparatus as described above.

In a further embodiment, destruction of target cells in blood may be carried out in-situ within the body of the subject by providing particles as above and applying an electric field to a region of the circulatory system through which the target cells pass, carried in the blood. Flexible electrode apparatus similar to that shown in FIG. 12c may attached to the body and used to apply a field to for example a region of blood vessel or other perfused area, so as to effect gradual removal of target cells as they pass through the field.

The invention has applications in biological processes, for example in cell culture. By selectively destroying target cells and leaving non-target cells unharmed, a mixed population can be purified of the target cells, for example when these are a minority contamination, or if the non-target cells are a desired minority cell type, the population can be enriched in non-target cell type by selective destruction of the target cells. Such methods have application in for example purification of the cell therapy product, for example in removing residual undifferentiated cells from a population of desired differentiated cells, or for selecting a non-target cell for further expansion by selectively removing the majority target cells from culture.

Figure 15A:
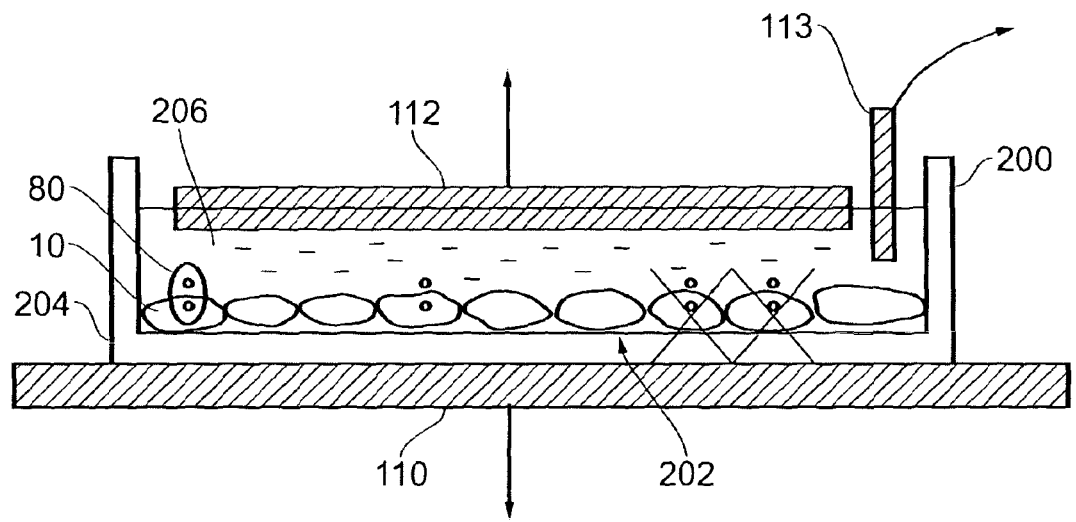
FIG. 15a shows an alternative embodiment, with a cell culture of attached cells and particles added to the culture, and in which a field is applied across the cell layer, so that target cells are affected and non-target cells are unaffected.

FIG. 15a shows a further embodiment of the apparatus of the invention, adapted for use in a biological process, here the cell culture of attached cells in an apparatus 200. In FIG. 15a cells 10 are cultured on a surface 202 within a container 204, in a medium 206. Particles are added to the medium and allowed to associate with the cells in a manner as described for previous embodiments. A field is then applied across one or more cells, in preferred embodiments across the thickness of the cell layer as shown, either over the whole region of the cell layer, or over specific sub-regions. The field is chosen so that target cells undergo cell death by non-thermal means mediated by the particles, such as by irreversible electroporation, while non-target cells are unaffected or affected to a lesser degree. The field may be applied in some embodiments by a first planar electrode 110 and second planar electrode 112. A first electrode might be mounted on or formed as part of the container 204. The second electrode is then preferably moveable or removable so as to access the interior of the container. The second electrode may be in contact with the medium, and may be insulated from it. Alternatively, the second electrode may be in electrical connection with the medium. The second electrode may alternatively be a probe-type electrode 113, which may be in electrical contact with the medium, the medium in some embodiments being conductive so as to provide a common potential over the upper surface of the cell layer. Alternatively the probe electrode may be insulated from the medium, and may be positionable over a region of the culture or over a single cell to localise the effect of the field. Such a probe electrode may be formed for example from a wire, or a tube or glass pipette filled with conducting liquid. While a single surface and a single layer of cells is shown in FIG. 15a, the invention is applicable to other known forms of container with single or multiple culture surfaces.

Figure 15B:
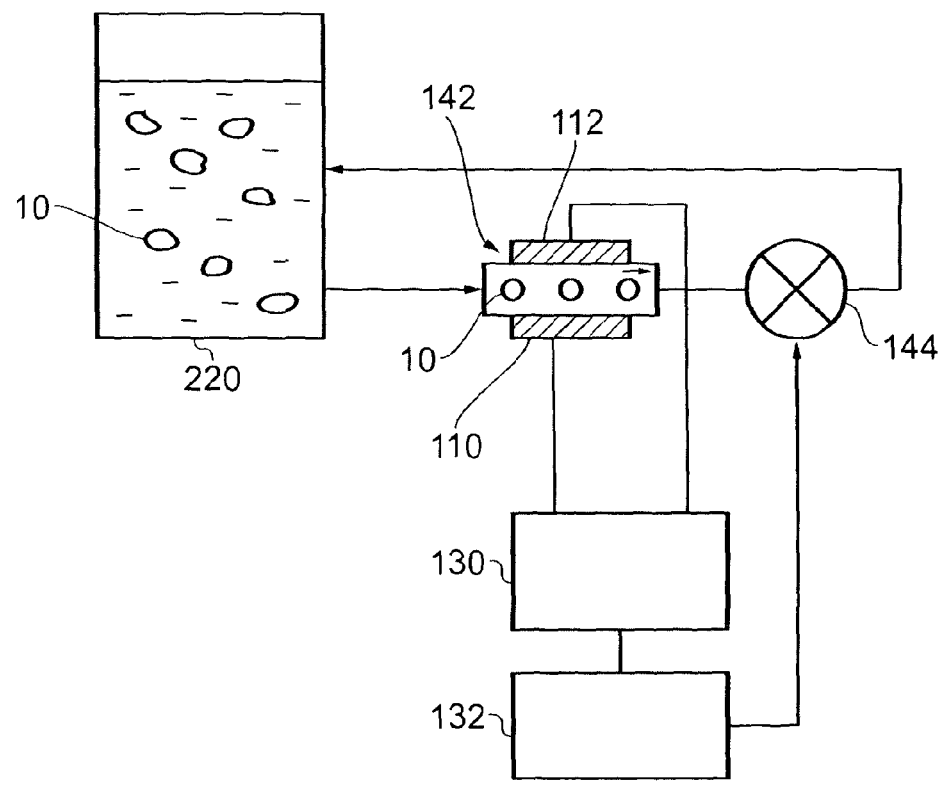
FIG. 15b is a diagrammatical view of a cell culture of cells in suspension in a bioreactor, and shows particles mixed with cells in a liquid medium, flowing through a flow cell in which cells are exposed to a field before being returned to the bioreactor.

FIG. 15b shows a further embodiment of an apparatus according to the invention, adapted to apply the invention to cell culture in suspension. Cells are cultured in suspension in a bioreactor 220. Particles are mixed with cells in medium, flowed through a flow cell 142 in which they are exposed to a field. Target cells are destroyed selectively as described earlier. The suspension depleted in the target cell may then be returned to the bioreactor. Particles may be added to the medium in the bioreactor, or in the flow system outside the bioreactor. An incubation time may be provided to allow particles to associate with the target cells. A suitable flow cell may be as described with respect to FIG. 14, for example a planar structure with electrodes on either side of a flow space, or a tubular structure with a concentric cylindrical electrode arrangement. More than one flow space may be provided in parallel, each with a pair of electrode surfaces one each side of the space, for example a stack of electrode pairs with flow spaces between them, with common inlet and outlet manifolds. The electrode potentials are provided by a device 130 under control of a programmable unit 132. Flow may be continuous or intermittent, so providing a batch process. Flow may be provided by a pump or flow controller 144, preferably under control of a control means associated with the device or (as shown) the programmable unit.

Figure 16:
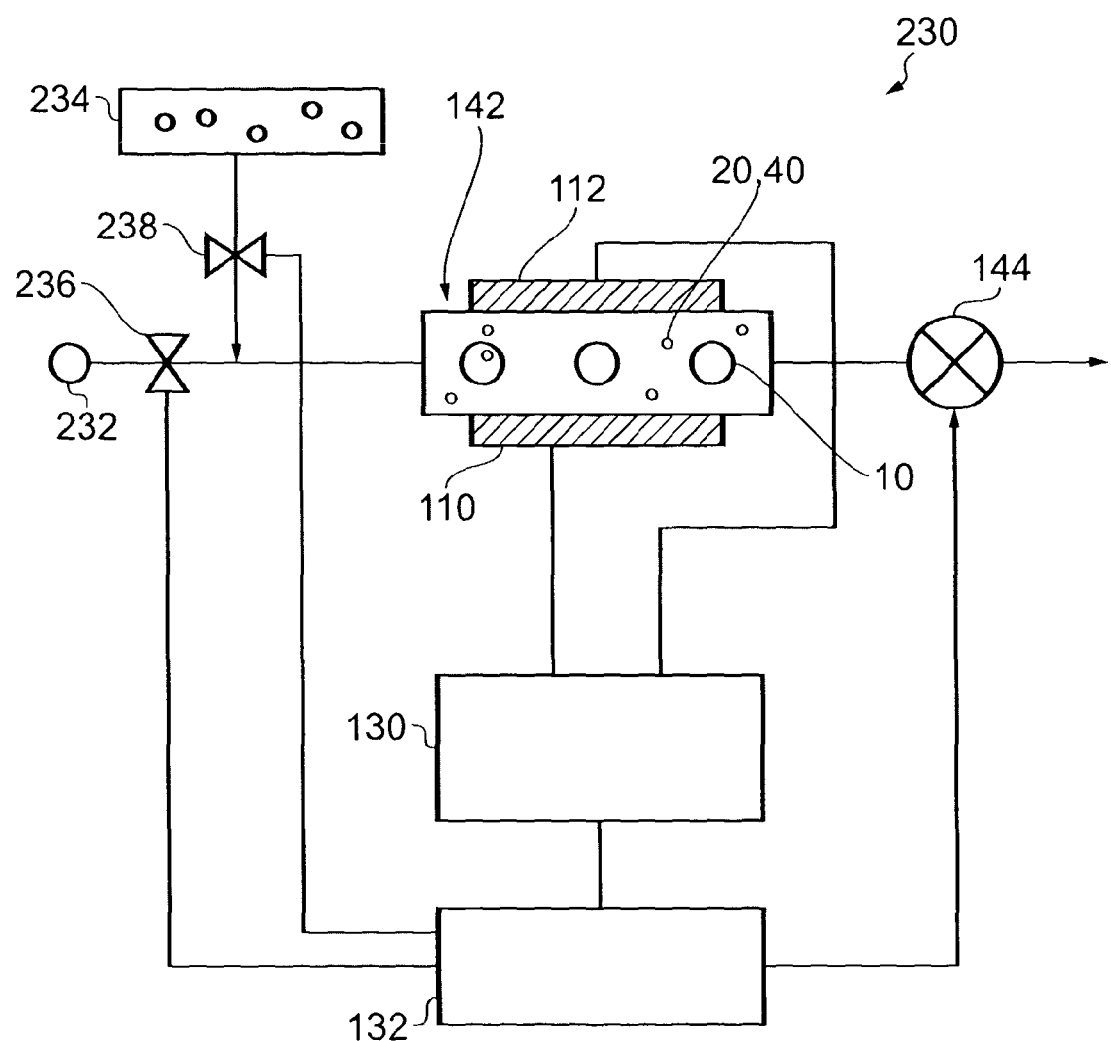
FIG. 16 is a diagrammatical view of an alternative embodiment of the invention adapted for sample processing, for example for use in diagnostics.

FIG. 16 shows an apparatus adapted to apply the method of the invention to sample processing, for example in diagnostics, the invention providing an improved means of cell lysis to allow release of cell contents into a medium for analysis, for example, DNA, RNA, proteins or other cell contents or components. A fluidic system 230 is provided comprising an inlet port 232, a flow cell 142 having means to apply a field to the contents of the flow cell, a supply of particles 234 connected to the flow system, and a flow means such as a pump 144. A sample containing cells is drawn through an inlet port 232, particles are mixed into a sample from a reservoir 234, allowed to associate with the cells, and then a field is applied in a flow cell 142. The field is provided by electrodes associated with the flow cell, controlled by the device 130 and the process may be controlled by a control means associated with the programmable unit 132, controlling the pump 144 and valves 236 and 238. The apparatus and method may be applied to lysing of all cell types within the sample by using particles adapted to associate with a wide range of cell types, or to lyse target cells selectively be means of targeted particles as described above.

Particles may be targeted to target cells by means of ligands adapted to bind to target molecules, for example cell receptors. Receptor-mediated endocytosis is known, in which particles bound by ligands to cell receptors are engulfed by the cell. Particles may be adapted by means of size, shape and ligand coating to be taken into cells by endocytosis or to be taken in to a lesser extent while remaining bound to the cell surface. For suitable particle sizes and morphology see for example Decuzzi and Ferraro US2010/029785; Zhang et al. Adv. Mater. 2009 vol. 21 p. 419-424; Muro et al. Molecular Therapy 2008 vol. 16 p. 1450-58.

In preferred embodiments of the invention, particles are used that provide suitable values of the following properties: rate of binding to a target cell membrane; affinity of binding; rate of endocytosis and rate of degradation of particles by lysosomes once inside the cell. These will depend in general on the size, shape and material of the particle and the nature and coverage of the ligands forming part of the coating.

Embodiments may comprise particles of types adapted to the target cell type and the mode of administration and may comprise particles of dimensions chosen from a range. Particles below 0.1 μm diameter are taken up readily by endocytosis and may be taken up in large numbers by target cells. Some embodiments of the invention comprise particles that in use tend to provide up to around ten particles within a target cell; in other embodiments up to around several tens, or in further embodiments up to around several hundred or over 1000 particles within a target cell. Larger particles up to around 1 um diameter may be taken up in smaller numbers, and some embodiments comprise particle types that in use tend to provide up to around 10 particles in a cell, in further embodiments 1 to 5 particles. Particles of greater than 1 um diameter may also be taken up in small numbers by a cell and may used in some embodiments. Preferably particles are adapted to control the rate of endocytosis. For example, spherical particles undergo endocytosis more readily than larger aspect ratio, for example disc-shaped or elliptical particles, or rod-shaped particles.

In embodiments of the invention particles have a characteristic maximum dimension in the range 10 nm to 5 um. In a preferred embodiment at least one particle type has a maximum dimension of 0.1 um or less. Preferably, a first particle type intended to be taken into the cell is of low aspect ratio, for example spherical, and small, for example 1 um or less in largest dimension, more preferably less than 500 nm and in some embodiments may be less than 100 nm in largest dimension, though larger and non-spherical particles are within the scope of the invention. In preferred embodiments where a second particle type is provided, intended to remain outside the cell membrane without promoting endocytosis, the second particle is preferably large, for example greater than 50 nm in largest dimension, more preferably greater than 100 nm, more preferably still greater than 500 nm in largest dimension.

In a preferred embodiment one or both of a first and a second particle comprise a gold microsphere of order 1 um diameter. In a further preferred embodiment one or both of the first and second particle comprise a gold nanosphere 40 to 60 nm in diameter. In a particularly preferred embodiment, at least a particle adapted to associate with the exterior of the cell membrane comprises a gold nanorod.

The first or the second particle types in some embodiments are non-spherical. For example, particles may be polyhedral, for example metal nanoprisms such as gold nanoprisms, elongated, for example elliptical, rod-like, tubular or may be formed from a cluster or agglomeration of smaller particles. A first particle adapted to enter the target cell and a second particle adapted to bind outside may be different sizes and different morphologies, preferably with the second particle having a larger maximum dimension and higher aspect ratio than the first.

In preferred embodiments, the method of the invention comprises time interval(s) according to the nature of the particles in use, to allow sufficient time for the particles to reach their intended location and binding configuration but preferably not so long that internal particles suffer lysosomal degradation or particles intended to remain external undergo unwanted endocytosis.

Embodiments of the invention comprise particles formed from materials as described herein and materials similar to these as may be understood by the skilled person. Preferably particles have a core comprising a material that is a dielectric, ideally having a high relative permittivity, or that is conductive or semiconductive. Preferably particles comprise a material having a high permittivity compared with the effective permittivity of the environment or medium in which they are intended to be located in use (in this context, the terms medium and environment are used interchangeably herein). However, in embodiments, the invention is not limited to high permittivity particles, rather may derive its effect from the co-operative effects of lower permittivity particles.

The material may have a permittivity selected from within a range according to the embodiment. A typical relative permittivity of a cell membrane is around 11.5 (see e.g.

Raffa et al WO-A-2008/062378). Therefore in some embodiments a particle comprises a material having a relative permittivity of greater than or approximately equal to 11. In further embodiments a particle comprises a material having a relative permittivity of 20 or above, and in further embodiments greater than or approximately equal to that of blood or physiological saline (typical value 88). In further embodiments a particle may comprise a conductive material, for example having a semiconductive or conductive core, and in preferred embodiments the conductivity will be greater than or approximately equal to that of then environment in which it is intended to be located. Magnetic particles as used in magnetic separations comprise appropriate materials for use in embodiments of the invention, for example commercially-available magnetic separation particles, for example comprising a core of Fe3O4.

In alternative embodiments, particles of lower permittivity than the surrounding medium or environment are used, for example contributing to field enhancement by localisation external to the cell membrane as described in relation to FIG. 6e. In these embodiments, the relative permittivity of a core material of the particle may be less than around 88, preferably less than 20, and may have a value less than 5. For example, particles comprising SiO2 or similar low permittivity oxides, or other dielectrics, may be applied in some embodiments of the invention, with the appropriate applied electric field strength for those particles to achieve cell death ideally by means of irreversible electroporation.

The invention ideally comprises particles, and apparatus and compositions containing particles, that may be selected by a skilled person based on the foregoing, together with choice of an appropriate field strength and waveform.

The term cell or target cell refers to a biological form of life comprising for example, a microorganism, a virus, or an eukaryote cell.

The eukaryote cell may e.g. be a plant cell, a plant spore, an animal cell such as mammal cell.

The mammal cell may e.g. be a human cell such as:

A keratinizing epithelial cell, such as a keratinocyte of epidermis, basal cell of epidermis (stem cell), keratinocyte of finger and toe nails, basal cell of nail bed (stem cell), hair shaft cell, hair root sheath cell, hair matrix cell (stem cell). Additionally a cell may be a wet stratified barrier epithelia such as, surface epithelial cell of stratified squamous epithelium of cornea, tongue, oral cavity, esophagus, anal canal, distal urethra, vagina or basal cell of these epithelia (stem cell), or cell of urinary epithelium (lining bladder and urinary ducts).

Other types of cell are an epithelial cell specialized for exocrine secretion such as cells of the salivary glands, cell of von Ebner's gland in tongue, cell of mammary gland, cell of lacrimal gland, cell of ceruminous gland of ear, cell of eccrine sweat gland, cell of apocrine sweat gland, cell of gland of Moll in eyelid, cell of sebaceous gland, cell of Bowman's gland in nose, cell of Brunner's gland in duodenum, cell of seminal vesicle, cell of prostate gland, cell of bulbourethral gland, cell of Bartholin's gland, cell of Littre's gland, cell of endometrium of uterus, isolated goblet cell of the respiratory and digestive tracts, mucous cell of the lining of the stomach, zymogenic cell of gastric gland, oxyntic cell of pancreas, Paneth cell of small intestine, type II pnemocyte of lung.

Other types of cell are cell specialized for secretion of hormones such as cells of anterior pituitary secreting growth hormone, follicle-stimulating hormone, luteinizing hormone, prolactin, adrenocorticotropic hormone, thyroid-stimulating hormone or cell of intermediate pituitary secreting melanocyte-stimulating hormone, or cell of posterior pituitary secreting oxytocin or vasopressin, or cell of gut and respiratory tract secreting serotonin, endorphin, somatostatin, gastrin, secretin, cholecystokinin, insulin, glucagon or bombesin.

Other types of cell are cell of the thyroid gland secreting thyroid hormone or calcitonin, a cell of the parathyroid gland secreting parathyroid hormone or an oxyphil cell, a cell of adrenal gland secreting epinephrine, norepinephrine, steroid hormones such as mineralocorticoids or glucocorticoids, a cell of gonads secreting testosterone (Leydig cell of testis) estrogen (theca interna cell of ovarian follicle), progesterone (corpus luteum cell of ruptured ovarian follicle), a cell of juxtaglomerular apparatus of kidney secreting rennin, an epithelial absorptive cell in the gut, exocrine glands, and urogenital tract such as brush border cell of intestine (with microvilli), striated duct cell of exocrine glands, gall bladder epithelial cell, brush border cell of proximal tubule of kidney, distal tubule cell of kidney, nonciliated cell of ductulus efferens, epididymal principal cell or epididymal basal cell.

Other types of cell are a cell specialized for metabolism and storage such as hepatocyte, liver lipocyte or fat cell, an epithelial cell serving primarily a barrier function, lining the lung, gut, exocrine glands, and urogenital tract such as type I pneumocyte cell (lining air space of lung), pancreatic duct cell (centroacinar cell), nonstriated duct cell of sweat gland, salivary gland, mammary gland etc. (various), parietal cell of kidney glomerulus, podocyte of kidney glomerulus, cell of thin segment of loop of Henle (in kidney), collecting duct cell (in kidney), duct cell of seminal vesicle, prostate gland, etc. (various), an epithelial cell lining closed internal body cavities such as vascular endothelial cells of blood vessels and lymphatics (fenestrated, continuous, splenic), synovial cell (lining joint cavities, secreting largely hyaluronic acid), serosal cell (lining peritoneal, pleural, and pericardial cavities), squamous cell lining perilymphatic space of ear, cells lining endolymphatic space of ear, squamous cell columnar cells of endolymphatic sac (with microvilli or without microvilli), "dark" cell, vestibular membrane cell, stria vascularis basal cell, stria vascularis marginal cell, cell of Claudius, cell of Boettcher, choroid plexus cell (secreting cerebrospinal fluid).

Other types of cell are squamous cell of pia-arachnoid, cells of ciliary epithelium of eye (pigmented or nonpigmented), corneal "endothelial" cell, a ciliated cell with propulsive function of respiratory tract, of oviduct and of endometrium of uterus (in female), of rete testis and ductulus efferens (in male) or a cell of a central nervous system (ependymal cell lining brain cavities), a cell specialized for secretion of extracellular matrix such as epithelial ameloblast (secreting enamel of tooth), epithelial planum semilunatum cell of vestibular apparatus of ear (secreting proteoglycan), interdental cell of organ of Corti (secreting tectorial "membrane" covering hair cells of organ of Corti), nonepithelial (connective tissue) such as fibroblasts (various—of loose connective tissue, of cornea, of tendon, of reticular tissue of bone marrow, etc.), pericyte of blood capillary, nucleus pulposus cell of intervertebral disc, cementoblast/cementocyte (secreting bonelike cementum of root of tooth), odontoblast/odontocyte (secreting dentin of tooth), chondrocytes of hyaline cartilage of fibrocartilage of elastic cartilage, osteoblast/osteocyte, osteoprogenitor cell (stem cell of osteoblasts), hyalocyte of vitreous body of eye or stellate cell of perilymphatic space of ear.

Other types of cell are: a contractile cell such as skeletal muscle cells (red (slow), white (fast), inter-mediate, muscle spindle—nuclear bag, muscle spindle—nuclear chain, satellite cell (stem cell), or heart muscle cells (ordinary, nodal, Purkinje fiber), or smooth muscle cells (various), or myoepithelial cells of iris or of exocrine glands.

Other types of cell are a cell related to blood or the immune system such as red blood cell, megakaryocyte, macrophages and related cells (monocyte, connective-tissue macrophage (various), Langerhans cell (in epidermis), osteoclast (in bone), adendritic cell (in lymphoid tissues), microglial cell (in central nervous system)), neutrophil, eosinophil, basophil, mast cell, T lymphocyte (helper T cell, suppressor T cell, killer T cell), B lymphocyte (IgM, IgG, IgA, IgE), killer cell or stem cells and committed progenitors for the blood and immune system (various), a cell with sensory and transducing functions such as photoreceptors (rod, cones [blue sensitive, green sensitive, red sensitive], hearing (inner hair cell of organ of Corti, outer hair cell of organ of Corti), acceleration and gravity (type I hair cell of vestibular apparatus of ear, type II hair cell of vestibular apparatus of ear), taste (type II taste bud cell), smell (olfactory neuron, basal cell of olfactory epithelium (stem cell for olfactory neurons)), blood pH (carotid body cell [type I, type II]), touch (Merkel cell of epidermis, primary sensory neurons specialized for touch (various)), temperature (primary sensory neurons specialized for temperature [cold sensitive, heat sensitive]), pain (primary sensory neurons specialized for pain (various)), configurations and forces in musculo-skeletal system (proprioceptive primary sensory neurons (various)).

Other types of cell are an autonomic neuronal cell (cholinergic (various), adrenergic (various), peptidergic (various)), a supporting cells of sense organs and of peripheral neurons such as supporting cells of organ of Corti (inner pillar cell, outer pillar cell, inner phalangeal cell outer phalangeal cell, border cell, Hensen cell), or a supporting cell of vestibular apparatus, or a supporting cell of taste bud (type I taste bud cell), or a supporting cell of olfactory epithelium, or a Schwann cell, or a satellite cell (encapsulating peripheral nerve cell bodies) or a enteric glial cell; a neuronal or glial cells of the central nervous system such as neurons (huge variety of types—still poorly classified), glial cells (astrocyte (various), oligodendrocyte).

It is appreciated that reference to cell includes the following cells: a lens cell such as anterior lens epithelial cell, lens fiber (crystallin-containing cell), or pigment cell such as melanocyte or retinal pigmented epithelial cell, a germ cell such as oogonium/oocyte, spermatocyte, or spermatogonium (stem cell for spermatocyte), a nurse cell such as ovarian follicle cell, sertoli cell (in testis), or thymus epithelial cell, Other types of cell are n interstitial cell such as interstitial cells of Cajal in the gastro-intestinal system, or interstitial cell of the kidney or other organs with pacemaker functions.

The microorganism may e.g. be selected from the group consisting of an archeal microorganism, a eubacterial microorganism or a eukaryotic microorganism, the microorganism may be selected from the group consisting of a bacterium, a bacterial spore, a virus, a fungus, and a fungal spore.

In a preferred embodiment of the invention, the microorganism is hosted inside a mammalian cell which is serving as a reservoir for the infection.

In a preferred embodiment of the invention, the microorganism is resistant to common chemotherapies such as anti-biotics such as but excluded too methicillin-resistant *Staphylococcus aureus* (MRSA), vancomycin-resistant *Staphylococcus aureus* (VRSA), penicillin resistant *Streptococcus*, anti-biotic resistant strains of *Mycobacterium tuberculosis*, penicillin resistant *Enterococcus*, multi-drug resistant *Pseudomonas aeruginosa*, clindamycin (or fluoroquinolone) resistant *Clostridium difficile* (diarrheal disease) and multi-drug resistant *Escherichia coli*.

Further applications of the invention are within biological processes, cell biology research, detection of cells in a sample and diagnostics. The following features and details may apply to each of the embodiments described above, and combinations of them may be used in any given embodiment as will be apparent to the skilled person.

Although reference has been made to cell lysis, it is understood that the method apparatus and systems herein described are capable of being modified and used to arrest cell reproduction, specifically uncontrolled cell reproduction that is encountered in tumours.

Ideally a control means, operating under control of instructions in the form of software and using data derived from a look-up table, the control means applies a variable potential to the first and second electrodes, in accordance with the data and under instruction from the software, whereby in use, target cells within the electric field are killed and non-target cells remain unharmed.

A preferred embodiment of the apparatus may be portable and worn as a belt and is usable with the method of the invention.

Furthermore it is understood that references herein to a method are taken to encompass a corresponding apparatus and vice versa.

Other aspects of the invention provide for the following embodiments:

1. Wherein a plurality of cells are killed by apoptosis.
2. Wherein the particle is adapted to bind or adhere to the cell wall.
3. Wherein the cell membrane is of the order of 10 nm thick.
4. Wherein the target molecule is a biomarker.
5. Wherein the target molecule is from the groups comprising: lipids, carbohydrates, nucleic acids or proteins.
6. Wherein the nucleic acid comprises chromosomal DNA and/or plasmid DNA, and/or any type of RNA.
7. Wherein the protein is from the group comprising: enzymes, structural proteins, transport proteins, in channels, toxins, hormones or receptors.
8. Wherein the cell targeting is achieved by means of antibodies, aptamers, and/or ligands on the surface of the particle.
9. Wherein the ligand comprises more than one species to increase capture affinity.
10. Wherein for an elongated particle, the coating is located in a specific region at one end of the particle.
11. Wherein apparatus for treatment of a disease condition in a subject using particles or nanoparticles and time-varying electromagnetic or electric fields, characterised in that a means if provided to introduce a market to the interior of a target cell and a means is provided for exposing the target cell to an electric field sufficient to cause irreversible electroporation of the cell.
12. Wherein the apparatus is used to treat neoplasia, cancerous cells or infections, such as those caused by fungi, viral or other microorganisms.
13. Wherein the means to introduce particles to the interior of the cell includes a particle delivery device that administers particles to the target cells.
14. Wherein the means of administering is through topical or systemic administration.
15. Wherein the apparatus incorporates means to deliver a first particle type adapted to enter a target cell, and a second particle type adapted to bind to a target molecule on the exterior of a target membrane.

16. Wherein the particles are administered systemically through body fluid such as blood, lymph, cerebrospinal fluid.

17. Wherein the target cells comprise bacteria, spores, vira or mammalian cells such as leukemic or virally infected cells within the body fluid.

18. Wherein the target cells are localised such as in a local seat of infection, or a region of neoplasia or a tumour.

19. Wherein the particles are administered by injection and/or infusion, and/or electroporation through skin and/or inhalation, and/or absorption through mucal membranes, and/or via the digestive tract.

20. Wherein devices for administration include a syringe, cannula, catheter, inhaler, implanted release device, capsule and/or ingestible preparation.

21. Wherein there is provided a means to expose the target cells to a variable electric or electromagnetic field comprising: at least a first and a second electrode and a control means for applying a variable potential to the first and second electrodes, whereby target cells within the electric field are killed and non-target cells remain unharmed. The field strength may be chosen according to the nature of the disease condition, the nature of the particles, and the proportions of target and non-target cells that are to be destroyed on average in a given treatment.

22. Wherein there is provided a method for treatment of a disease in a subject by means of destruction of target cells within the subject, comprising the steps of:
a) administering particles to the subject, either systemically or topically in the region of the target cells, the particles being adapted to be taken up within the target cells;
b) allowing a chosen time interval to elapse so that at least one particle is taken up within at least one target cell; and
c) applying an electric field to a region of the subject within which one or more target cells are located in order to cause cell death of the targeted cells by predominantly non-thermal means.

23. Wherein particles are tracked within the body fluid by tracking means such as MRI, ultrasound, computer tomographic scanner.

Wherein a delay of greater than 10 minutes is provided between administration of the first and second particles 24. Wherein targeted cell lysis—comprising a particle inside cell and exposing to field sufficient to cause IEP 25. Wherein a device for treatment of a disease condition using particles and an electric field, characterised in that means is provided to introduce a particle inside a target cell and means is provided for exposing the target cell to a field sufficient to cause IEP.

26. Wherein a second particle outside the cell.

27. Wherein particles may have a coating that makes them selective for the target cell—one binds at membrane, one bind inside the cell.

28. Wherein a composition comprising plurality of particles adapted for use in method and system for causing death of target cell, eg. by IRE, particles adapted to enhance field.

The invention claimed is:

1. A method of causing targeted cell death by a non-thermal mechanism comprising:
introducing a first dielectric particle to an interior of an individual live target cell;
adhering a second dielectric particle on, or adjacent, an exterior surface of said individual live target cell; and
while said individual live target cell is live with said first dielectric particle interior of said individual live target cell, exposing said individual live target cell to a transient electromagnetic field for a sufficient time interval to cause said first dielectric particle to move toward said second dielectric particle to cause cell death, and thereafter removing said transient electromagnetic field.

2. A method of causing targeted cell death by a non-thermal mechanism according to claim 1, wherein:
a size of said first dielectric particle introduced to said interior of said individual live target cell, and a level of said transient electromagnetic field, are selected so as to cause sufficient movement of said first dielectric particle toward said second dielectric particle to cause irreversible electroporation of said individual live target cell.

3. A method of causing targeted cell death by a non-thermal mechanism, comprising:
introducing at least one first dielectric particle outside an individual live target cell;
introducing a second dielectric particle to an interior of said individual live target cell; and
while said individual live target cell is live with said second dielectric particle interior of said individual live target cell, exposing said individual live target cell to a transient electromagnetic field for a time interval sufficient to cause said first dielectric particle to move toward said second dielectric particle to cause cell death to said individual live target cell, and thereafter removing said transient electromagnetic field;
whereby said at least one first dielectric particle and said second dielectric particle act co-operatively to cause said cell death.

4. A method of causing targeted cell death by a non-thermal mechanism according to claim 3, wherein:
said first dielectric particle and said second dielectric particle have a high permittivity with respect to at least one of a cell membrane of said individual live target cell and an environment surrounding said cell membrane.

5. A method of causing targeted cell death by a non-thermal mechanism according to claim 4, wherein:
said first dielectric particle and said second dielectric particle have a core comprising a conductive metal material.

6. A method of causing targeted cell death by a non-thermal mechanism according to claim 5, wherein said conductive metal material is selected from a group comprising:
iron;
an oxide of iron;
silver;
gold; and
platinum.

7. A method of causing targeted cell death by a non-thermal mechanism according to claim 3, further comprising:
coating at least one of said first dielectric particle and said second dielectric particle with a coating selective for a target molecule on or within said individual live target cell.

8. A method of causing targeted cell death by a non-thermal mechanism according to claim 3, wherein:
said second dielectric particle is introduced to said interior of said individual live target cell by endocytosis.

9. A method of causing targeted cell death by a non-thermal mechanism according to claim 8, wherein:

said endocytosis is promoted by a coating on at least one of said first dielectric particle and said second dielectric particle at least two particles.

10. A method of causing targeted cell death by a non-thermal mechanism according to claim 9, wherein:
said endocytosis is promoted by said coating on both of said first dielectric particle and said second dielectric particle.

11. A method of causing targeted cell death by a non-thermal mechanism according to claim 9, wherein:
a second one of said first dielectric particle and said second dielectric particle has a coating different from said coating on said at least one of said first dielectric particle and said second dielectric particle.

12. A method of causing targeted cell death by a non-thermal mechanism according to claim 9, wherein said coating includes at least one from the group comprising:
a ligand;
an antibody;
an aptamer;
a protein;
a nucleic acid; and
a peptide species.

13. A method of causing targeted cell death by a non-thermal mechanism according to claim 3, further comprising;
varying a strength of said transient electromagnetic field in dependence upon time.

14. A method of causing targeted cell death by a non-thermal mechanism according to claim 3, wherein;
varying a strength of said transient electromagnetic field in dependence upon space.

15. A method of causing targeted cell death by a non-thermal mechanism according to claim 3, wherein;
a mechanical force is exerted as a result of said first dielectric particle and said second dielectric particle moving relative to one another so as to stress or otherwise disrupt a membrane of said individual live target cell.

16. A method of causing targeted cell death by a non-thermal mechanism according to claim 3, further comprising:
using carbon nanotubes to enhance an electroporation effect.

17. A method of causing targeted cell death by a non-thermal mechanism according to claim 3, further comprising:
binding tumor specific antibodies to said first dielectric particle and said second dielectric particle.

18. A method of causing targeted cell death by a non-thermal mechanism according to claim 3, wherein:
a size of said first dielectric particle is in a range of 20 nm to 2 um.

* * * * *